US012465518B2

(12) United States Patent
Shoham-Hazon et al.

(10) Patent No.: US 12,465,518 B2
(45) Date of Patent: Nov. 11, 2025

(54) DEVICE AND METHOD FOR GENERATING A CHANNEL IN AN EYE TISSUE LAYER FOR TREATMENT OF OCULAR DISORDERS

(71) Applicant: Hexiris Inc., Dieppe (CA)

(72) Inventors: Nir Shoham-Hazon, Dieppe (CA); Houfar Sekhavat, Dieppe (CA)

(73) Assignee: Hexiris Inc., Dieppe (CA)

( * ) Notice: Subject to any disclaimer, the term of this patent is extended or adjusted under 35 U.S.C. 154(b) by 0 days.

(21) Appl. No.: 19/048,877

(22) Filed: Feb. 8, 2025

(65) Prior Publication Data

US 2025/0235351 A1 Jul. 24, 2025

Related U.S. Application Data

(63) Continuation of application No. PCT/CA2025/050086, filed on Jan. 23, 2025.

(Continued)

(30) Foreign Application Priority Data

Nov. 26, 2024 (GB) ..................................... 2417304

(51) Int. Cl.
*A61F 9/007* (2006.01)

(52) U.S. Cl.
CPC ...... *A61F 9/00736* (2013.01); *A61F 9/00781* (2013.01)

(58) Field of Classification Search
CPC ... A61F 9/00736; A61F 9/00781; A61B 10/02
See application file for complete search history.

(56) References Cited

U.S. PATENT DOCUMENTS 3,929,123 A 12/1975 Jamshidi
9,795,503 B2 10/2017 Perez Grossmann
(Continued)

OTHER PUBLICATIONS

International Search Report and Written Opinion for International Application No. PCT/CA2025/050086, mailed Mar. 13, 2025.

*Primary Examiner* — Ashley L Fishback
*Assistant Examiner* — Chima U Igboko
(74) *Attorney, Agent, or Firm* — MARSHALL, GERSTEIN & BORUN LLP

(57) ABSTRACT

Surgical treatment of glaucoma involves creation of a sclerocorneal drainage channel, ensuring long-lasting controlled fluid flow and reduced intraocular pressure. Limitations relate to collateral damage to adjacent structures and outcomes being heavily reliant on the surgeon's expertise. The device described herein addresses such shortcomings. The device comprises a body for grasping, a piercing member including a proximal segment and a distal segment, the distal segment including a piercing tip at a distal end thereof, and a distal stabilizer element extending from a distal end of the body, the distal stabilizer element including a lumen, wherein the piercing member is configured to reciprocate from a stored position, wherein the proximal segment is retracted within the stabilizer lumen and the piercing tip extends outwardly from the stabilizer, and an extended position, wherein the distal segment and at least a portion of the proximal segment extend outwardly from the stabilizer.

14 Claims, 20 Drawing Sheets

Related U.S. Application Data

(60) Provisional application No. 63/567,580, filed on Mar. 20, 2024, provisional application No. 63/623,894, filed on Jan. 23, 2024.

(56) References Cited

U.S. PATENT DOCUMENTS

| | | | | |
|---|---|---|---|---|
| 2001/0007925 | A1 | 7/2001 | Ritchart et al. | |
| 2011/0105944 | A1* | 5/2011 | Ohnishi ............. | A61B 10/0266 600/566 |
| 2012/0004573 | A1* | 1/2012 | Andrews ............ | A61B 10/0275 600/567 |
| 2013/0131547 | A1* | 5/2013 | Hardert .............. | A61B 10/0266 600/567 |
| 2020/0105944 | A1 | 4/2020 | Arthur et al. | |
| 2020/0129331 | A1* | 4/2020 | Lavi ................... | A61B 10/0266 |
| 2024/0122754 | A1 | 4/2024 | Sekhavat et al. | |

* cited by examiner

FIG. 8A
FIG. 8B
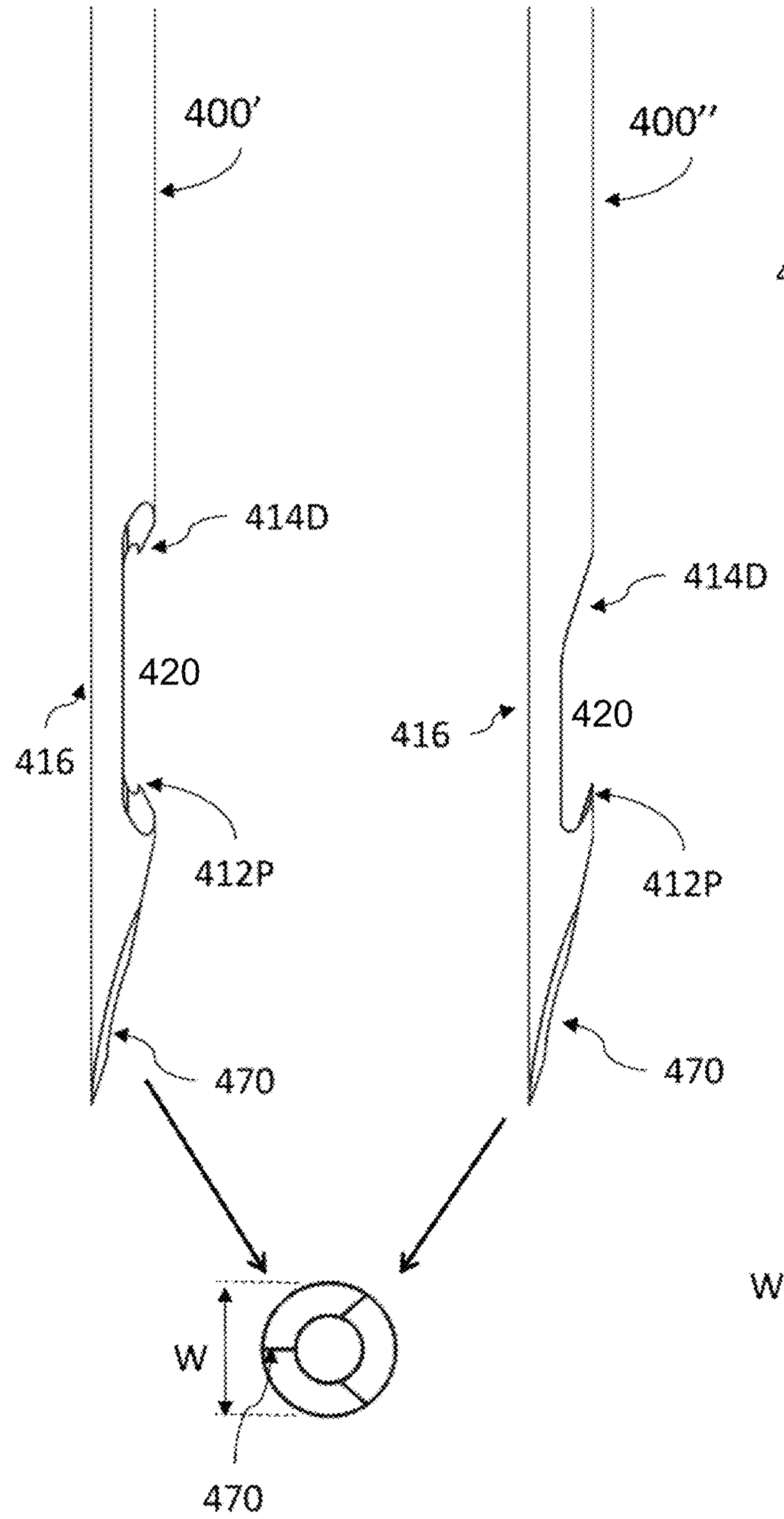
FIG. 8C
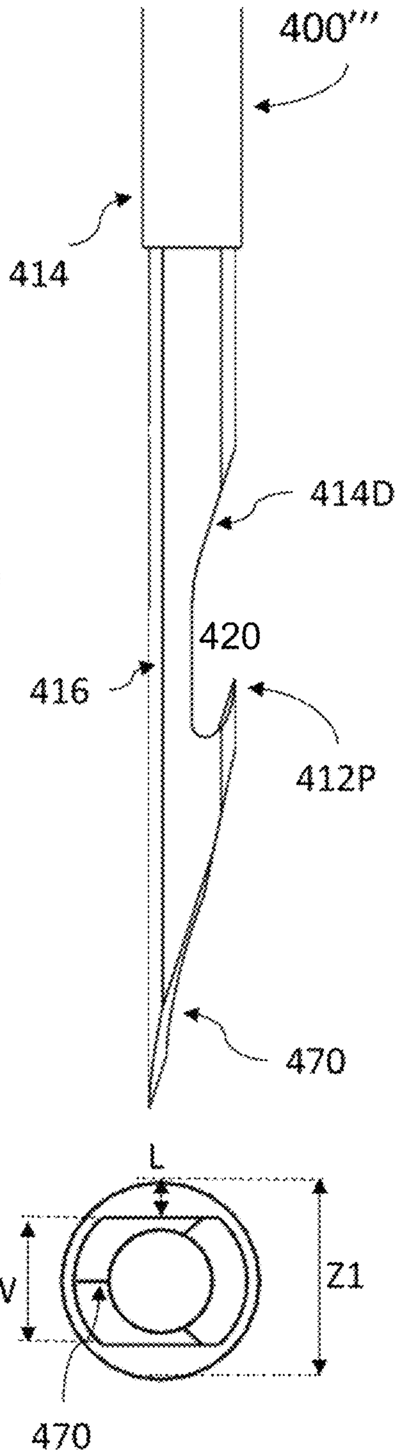

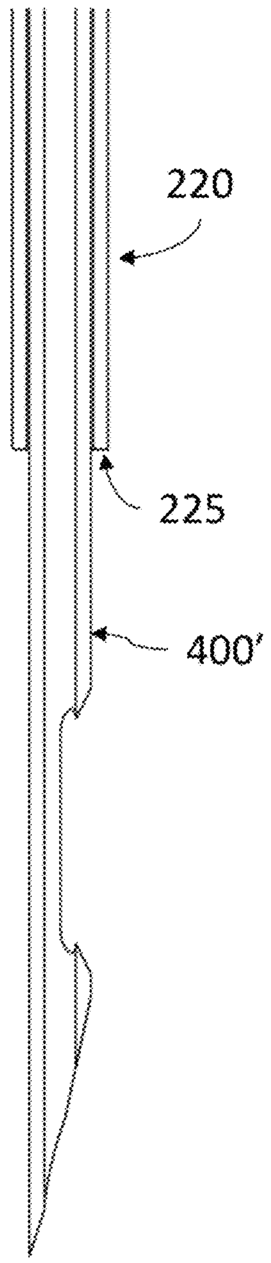
FIG. 8A1
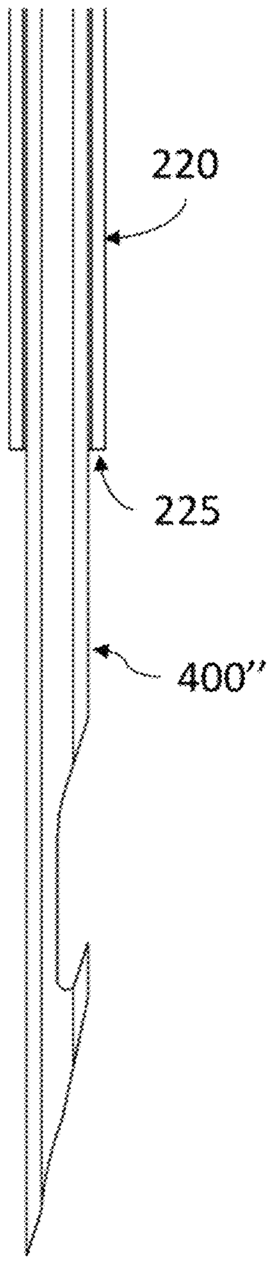
FIG. 8B1
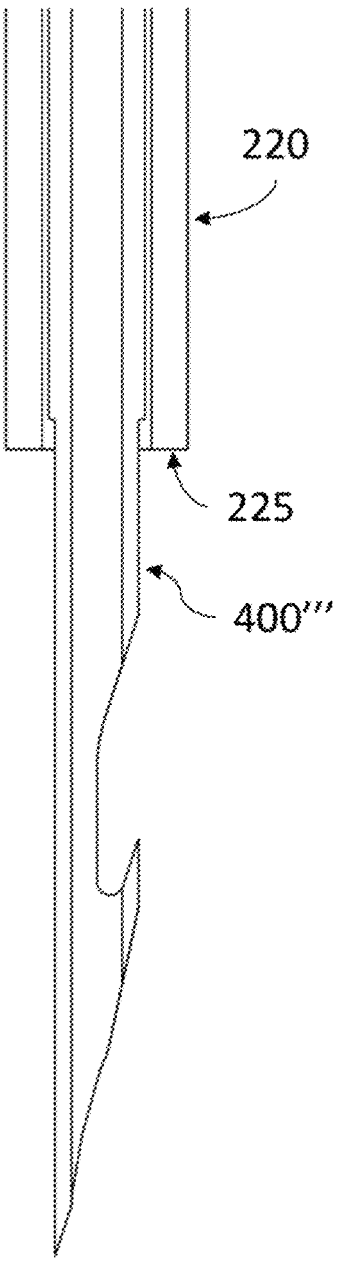
FIG. 8C1

DEVICE AND METHOD FOR GENERATING A CHANNEL IN AN EYE TISSUE LAYER FOR TREATMENT OF OCULAR DISORDERS

CROSS-REFERENCE TO RELATED APPLICATIONS

The present application is a continuation of International patent application no. PCT/CA2025/050086, filed Jan. 23, 2025, which claims the benefit of U.S. provisional patent application Ser. No. 63/623,894 filed on Jan. 23, 2024, U.S. provisional patent application Ser. No. 63/567,580 filed on Mar. 20, 2024, and Great Britain patent application serial number 2417304.9 filed on Nov. 26, 2024. The contents of each of the above-referenced documents are incorporated herein by reference in their entirety.

TECHNICAL FIELD

The present disclosure relates to a device and method for generating a channel in an eye tissue layer, in particular for treatment of ocular diseases or disorders.

BACKGROUND

Glaucoma is a group of eye diseases characterized by optic neuropathy, which can be associated with raised intraocular pressure (IOP). Glaucoma is the leading cause of irreversible blindness in the world. The primary goal of treatment is to lower the IOP by means of medicines or surgical procedures. Typically, surgical procedures and medical devices for treatment of eye disorders such as glaucoma are based on inside the eye (ab interno) or outside the eye (ab externo) approaches.

Surgical procedures have been proposed that involve creation of a sclerocorneal drainage channel, with the goal of ensuring long-lasting controlled fluid flow and reduced intraocular pressure.

For example, the use of a Kelly punch in ophthalmic procedures, while effective for creating precise channels or openings in ocular tissue, presents several limitations that impact its broader utility. Typically, this technique requires the creation of a conjunctival incision or the dissection of a scleral flap to access the target tissue. Using the Kelly punch, a small segment of scleral or trabecular tissue is excised to create a direct drainage pathway. This opening facilitates the outflow of aqueous humor from the anterior chamber to a subconjunctival bleb or other drainage areas. The scleral flap and conjunctival layers are carefully repositioned and sutured to ensure proper wound healing while maintaining the drainage pathway. Despite its clinical utility, the Kelly punch procedure presents certain limitations. For example, due to the manual nature of the procedure, the size and location of the created drainage channel can vary, potentially affecting efficacy. For example, the mechanical excision of tissue using a Kelly punch may result in collateral damage to adjacent structures, leading to inflammation or prolonged recovery—the outcomes are heavily reliant on the surgeon's expertise, with a steep learning curve required to achieve consistent results. Finally, the fixed design of the Kelly punch may not be ideal for all anatomical variations, reducing its applicability in complex or atypical cases.

To address these challenges, alternative methods such as the Minimally Invasive Micro Sclerostomy (MIMS) have been proposed in U.S. Patent Application Publication No. 2020/0129331 (Sanoculis). The MIMS technique eliminates the need for conjunctival or scleral flaps, creating a scleral channel using a minimally invasive device. While this approach reduces tissue trauma and shortens surgical recovery time, it is not without its limitations. The size and positioning of the channel are predetermined by the device, which is a relatively bulky surgical system composed of a multiuse control touchscreen, a foot-pedal and a disposable hand-piece unit. Additionally, achieving consistent outcomes can be challenging in patients with variations in scleral thickness or anatomy. The high initial cost of the MIMS device and the need for specialized training further limit its accessibility and adoption in certain clinical settings. Importantly, the MIMS™ system requires an operating room in case the conjunctiva or another eye tissue gets caught with the rotating cutting elements.

These shortcomings highlight the need for continued innovation to develop solutions that combine the precision of traditional methods with the reduced invasiveness and simplicity of newer approaches, without compromising flexibility or accessibility.

SUMMARY

This Summary is provided to introduce a selection of concepts in a simplified form that are further described below in the Detailed Description. This Summary is not intended to identify key aspects or essential aspects of the claimed subject matter.

In a broad aspect, the present disclosure relates to a device, comprising a body configured for grasping, a piercing member including a proximal segment and a distal segment, the distal segment including a piercing tip at a distal end thereof, and a distal stabilizer element extending from a distal end of the body, the distal stabilizer element including a lumen, wherein the piercing member is configured to reciprocate from (i) a stored position, wherein the proximal segment is retracted within the stabilizer lumen and piercing tip extends outwardly from the stabilizer, and (ii) an extended position, wherein the distal segment and at least a portion of the proximal segment extend outwardly from the stabilizer.

This device is particularly useful to form a drainage channel in an eye tissue layer. For example, a human eye.

In some embodiments, the device includes one or more of the following features:

- the proximal segment is connected to the distal segment via a connecting wall, wherein the connecting wall is configured to define an open cavity nested between a distal edge of the proximal segment and a proximal edge of the distal segment.
- the distal segment further includes a medial projection at a proximal end thereof, which includes a puncturing edge.
- the piercing tip and the medial projection are aligned along respective first and second longitudinal axes, the first and second longitudinal axes being parallel to one another.
- in the stored position, the piercing member is configured to perform a first cutting motion on a first surface of a tissue layer using the piercing tip.
- movement of the piercing member from the stored position to the extended position is configured to pierce the tissue layer such that the piercing tip traverses the tissue layer and extends beyond a second surface of the tissue layer, the first and second surfaces being opposite one another.
- movement of the piercing member from the extended position to the stored position is configured to perform a second cutting motion on the second surface of the tissue layer using the medial projection, the first and second cutting motions collectively forming a channel through the tissue layer.

the first and second cutting motions are coaxial.

the open cavity has a length sufficient for receiving a soft tissue segment corresponding to the channel, preferably the length is of from about 1.50 mm to about 2.50 mm.

the distal stabilizer element includes a distal end configured to abut against the first surface of the tissue layer after the first cutting motion.

further comprising an actuator assembly configured to cause the piercing member to reciprocate between the stored and the extended positions.

the actuator assembly includes a manually operable actuator, and wherein the actuator assembly is further configured to operatively couple the actuator to the piercing member.

the device body includes an internal surface defining an internal cavity, wherein the actuator assembly includes a stem extending through the internal cavity, and wherein the stem is configured to operatively couple the actuator to the piercing member.

the piercing member has one or more of the following: a length of from about 20 mm to about 50 mm; an external diameter size of from about 0.050 mm to about 3.000 mm; an inner cross section which is substantially circular with an internal diameter size of from about 0.040 mm to about 0.075 mm; and a body with a wall thickness of from about 0.050 mm to about 0.400 mm.

the piercing member includes a larger radius in a proximal portion and a reduced radius near a distal portion thereof.

In a broad aspect, the present disclosure relates to a method, comprising obtaining the device as described herein, and forming a drainage channel in an eye tissue layer with a reciprocal motion of the piercing member into and out of the eye tissue layer.

All features of exemplary embodiments which are described in this disclosure and are not mutually exclusive can be combined with one another. Elements of one embodiment can be utilized in the other embodiments without further mention. Other aspects and features of the present invention will become apparent to those ordinarily skilled in the art upon review of the following description of specific embodiments in conjunction with the accompanying Figures.

BRIEF DESCRIPTION OF THE DRAWINGS

A detailed description of specific exemplary embodiments is provided herein below with reference to the accompanying drawings in which:

FIG. 8A to FIG. 8C are non-limiting perspective views of different embodiments of the piercing member for use with the medical device of FIG. 2 for making a drainage channel in a patient eye, in accordance with embodiments of the present disclosure FIG. 8A1 to FIG. 8C1 are non-limiting perspective views corresponding to each of the embodiments of the piercing member of FIG. 8A to FIG. 8C1 shown with the stabilizer, in accordance with embodiments of the present disclosure.

Figure 1:
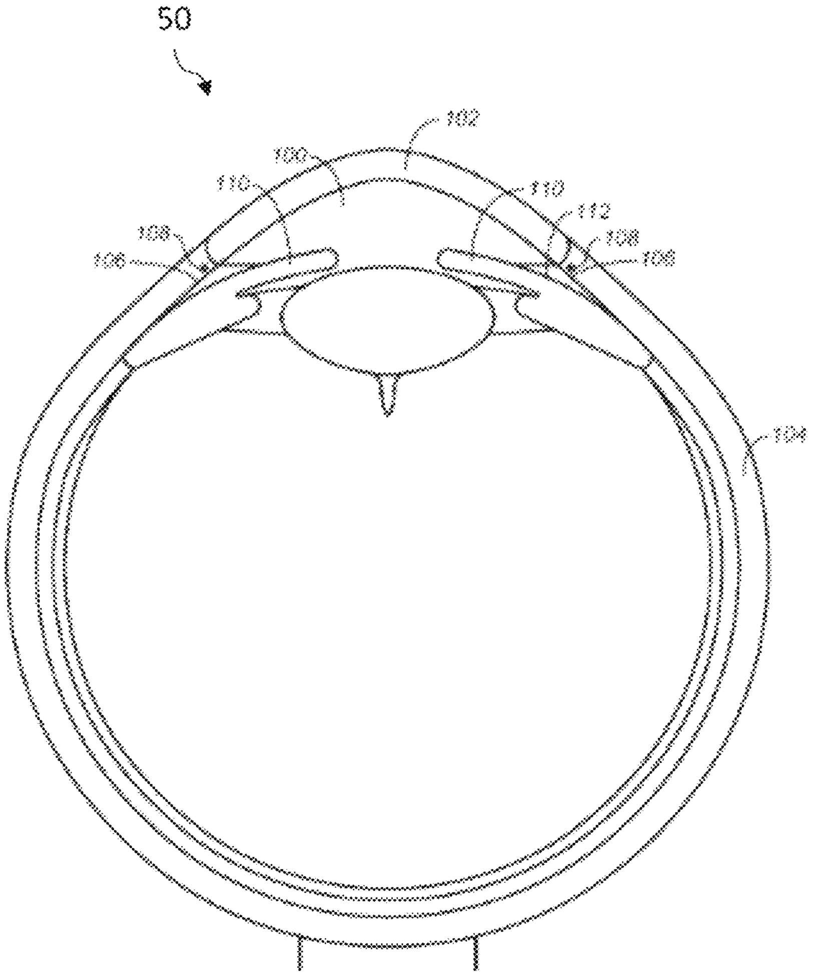
FIG. 1 is a cross sectional schematic diagram of a human eye.

In the drawings, exemplary embodiments are illustrated by way of example. It is to be expressly understood that the description and drawings are only for the purpose of illustrating certain embodiments and are an aid for understanding. They are not intended to be a definition of the limits of the disclosure.

DETAILED DESCRIPTION

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art considering the instant disclosure which variations and additions do not depart from the present technology. Hence, the following description is intended to illustrate some embodiments of the technology, and not to exhaustively specify all permutations, combinations, and variations thereof.

Described herein is a device configured to form a channel in a tissue layer. For example, a tissue layer of an eye for treatment of ocular disorders or diseases. For example, a drainage channel for reducing eye internal pressure. For example, the eye can be a human eye.

In some embodiments, the device is configured to form a drainage channel in an eye tissue layer with a reciprocal motion of a piercing member into and out of the eye tissue layer.

For example, forming the drainage channel strictly can involve axial cutting motions with the piercing member. Advantageously, forming the drainage channel does not include rotational cutting movements.

For example, forming the drainage channel can include a first axial cutting motion on a first surface of the tissue layer to form a first incision, and a second axial cutting motion on a second surface of the tissue layer to form a second incision, and remove a soft tissue segment thus forming the channel. For example, the first and second surfaces are on opposite sides of the tissue layer.

The reader will readily understand that in the present specification, an "axial cutting motion" means a cutting motion along an axis as opposed to a cutting motion using rotational movement.

In some embodiments, the medical device is configured to remove the soft tissue segment from an eye tissue layer interfacing the anterior chamber of the eye to enable drainage of excessive fluid from inside the anterior chamber of the eye.

In some embodiments, the medical device is configured to perform an ab externo perforation in the eye tissue layer.

In some embodiments, the medical device is configured to perform an ab interno perforation in the eye tissue layer.

In some embodiments, the medical device can be useful for treatment of glaucoma.

In some embodiments, the drainage channel is a stent-less functional channel, i.e., a tubeless channel.

Advantageously, the herein described medical device and method of use is useful to obtain a channel in an eye tissue layer interfacing the anterior chamber of the eye, without the need to create a conjunctival incision or a scleral flap. In other words, forming the drainage channel in the eye tissue layer is obtained by contacting the medical device on an intact eye tissue layer.

In some embodiments, the herein described procedure and medical device can be used to form a drainage channel in a tissue layer of an eye, where the drainage channel has a length of from about 1.0 mm to about 2.5 mm, including any values or ranges therein. For example, a length of about 1.0 mm, about 1.5 mm, about 2.0 mm, or about 2.5 mm.

The present inventors have surprisingly observed that commercial ophthalmologic medical devices or systems suffer from one or more drawbacks, which are more readily observed by medical practitioners when performing ophthalmological procedures, and offers at least one or more of the following advantageous features.

For example, the herein described medical device can be used in a clinical office setting, without the need for an operating room.

For example, the herein described medical device can be used to form a drainage channel in an eye tissue layer with axial cutting motions, i.e., without rotating cutting tools, thus minimizing injury risk to eye tissue that exist with rotating cutting tools.

For example, the herein described medical device allows more flexibility and ease of operation in terms of being configured for being held and operated with one hand, i.e., in contrast to existing bulky surgical MIMS™ system that requires being operated with the foot while being held with a hand.

For example, the herein described medical device allows more flexibility and ease of operation in terms of being usable with either left- or right-handed user (ambidextrous usage possible). The user may be a medical practitioner, such as an ophthalmologist.

For example, the herein described medical device can be a single use device, thus reducing sterilization requirements that are present for reusable systems.

For example, the herein described medical device and its associated usage methods discussed herein demonstrate notable efficacy and utility in the precise extraction of soft tissue. This is achieved by generating a well-defined, controlled channel within the tissue layer. It should be noted that a "channel" as used herein refers to a pathway formed within the tissue subsequent to the removal of a corresponding soft tissue segment from the body. Notably, no components, such as implants, are retained in the body to establish or sustain the integrity of the created channel.

For example, the channel generated with the herein described medical device can offer distinct advantages compared to other methods that involve the placement of implants within the tissue to ensure fluid drainage. This is because with the herein described medical device and associated usage methods discussed herein, nothing remains within the tissue except for the established void, hole, or channel that spans between the two sidewalls of the specific tissue layer, as applicable. To clarify, the resulting channel is essentially a hole traversing the tissue layer, devoid of any artificial tube or shunt within the target tissue. Consequently, the created channel can exhibit dynamic characteristics, functioning as a pressure regulator. The channel can have the capacity to adjust its drainage efficiency by altering its size in response to the pressure at both ends. In situations of increased pressure gradient, the channel opens or enlarges, and conversely, in decreased pressure gradient scenarios, the channel closes or reduces in size accordingly.

Such technical advantages of the medical device and procedure described herein will be more apparent to the person of skill in light of the present disclosure.

Eye Structures

Relevant structures of the eye will first be briefly described to provide background for the anatomical terms used herein.

FIG. 1 is a stylized depiction of a normal human eye 50. Certain anatomical details, well known to those skilled in the art, have been omitted for clarity and convenience. The anterior chamber 100 is shown as bounded on its anterior surface by the cornea 102. The cornea 102 is connected on its periphery to the sclera 104, which is a tough fibrous tissue forming the white shell of the eye. Trabecular meshwork 106 is located on the outer periphery of the anterior chamber 100. The trabecular meshwork 106 extends 360 degrees circumferentially around the anterior chamber 100. Located on the outer peripheral surface of the trabecular meshwork 106 is Schlemm's canal 108. Schlemm's canal 108 extends 360 degrees circumferentially around the meshwork 106. At the apex formed between the iris 110, meshwork 106, and sclera 104, is angle 112.

Medical Device

Figure 2:
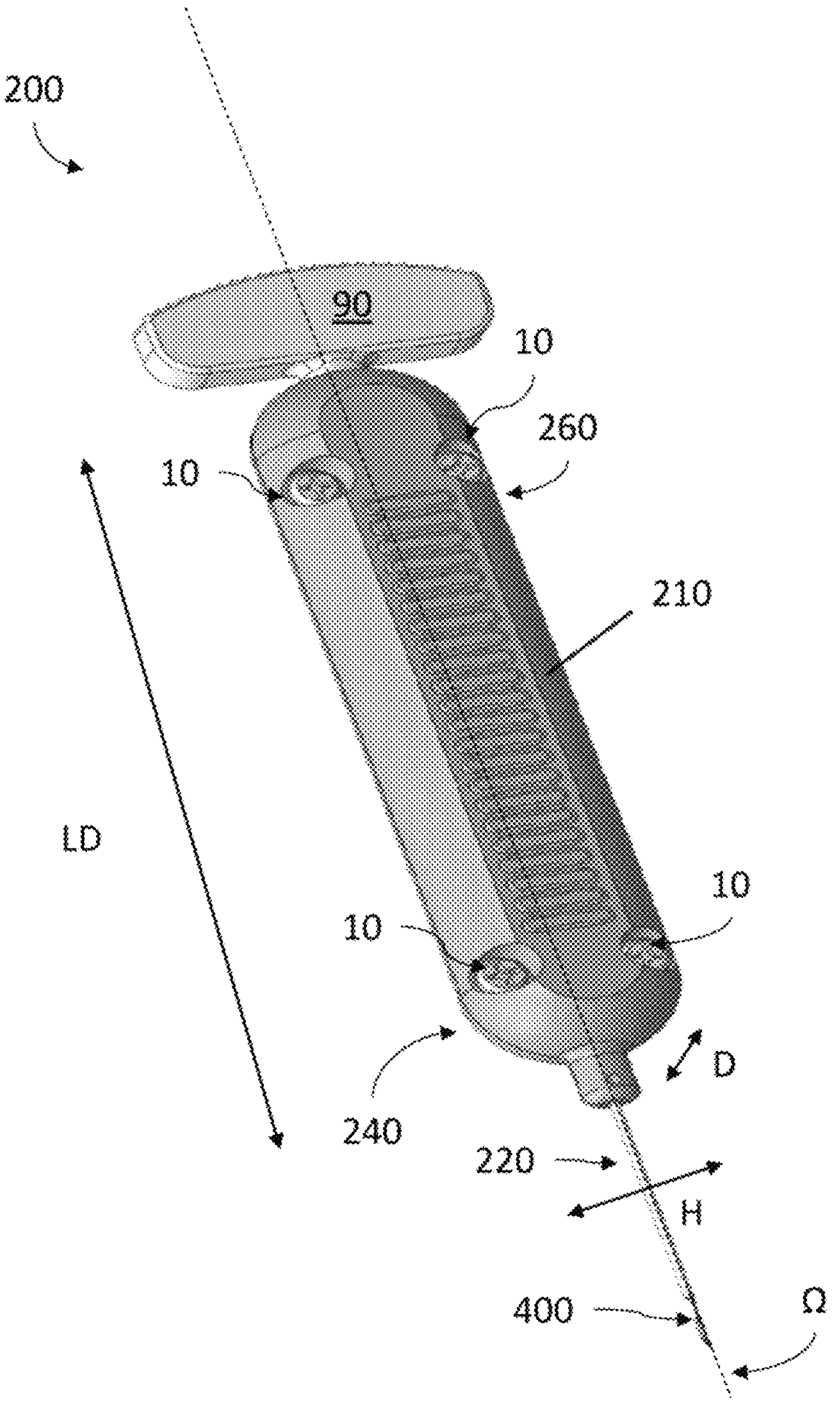
FIG. 2 is a non-limiting perspective view of an embodiment of a device for generating a channel in an eye tissue layer, in accordance with embodiments of the present disclosure.
Figure 10:
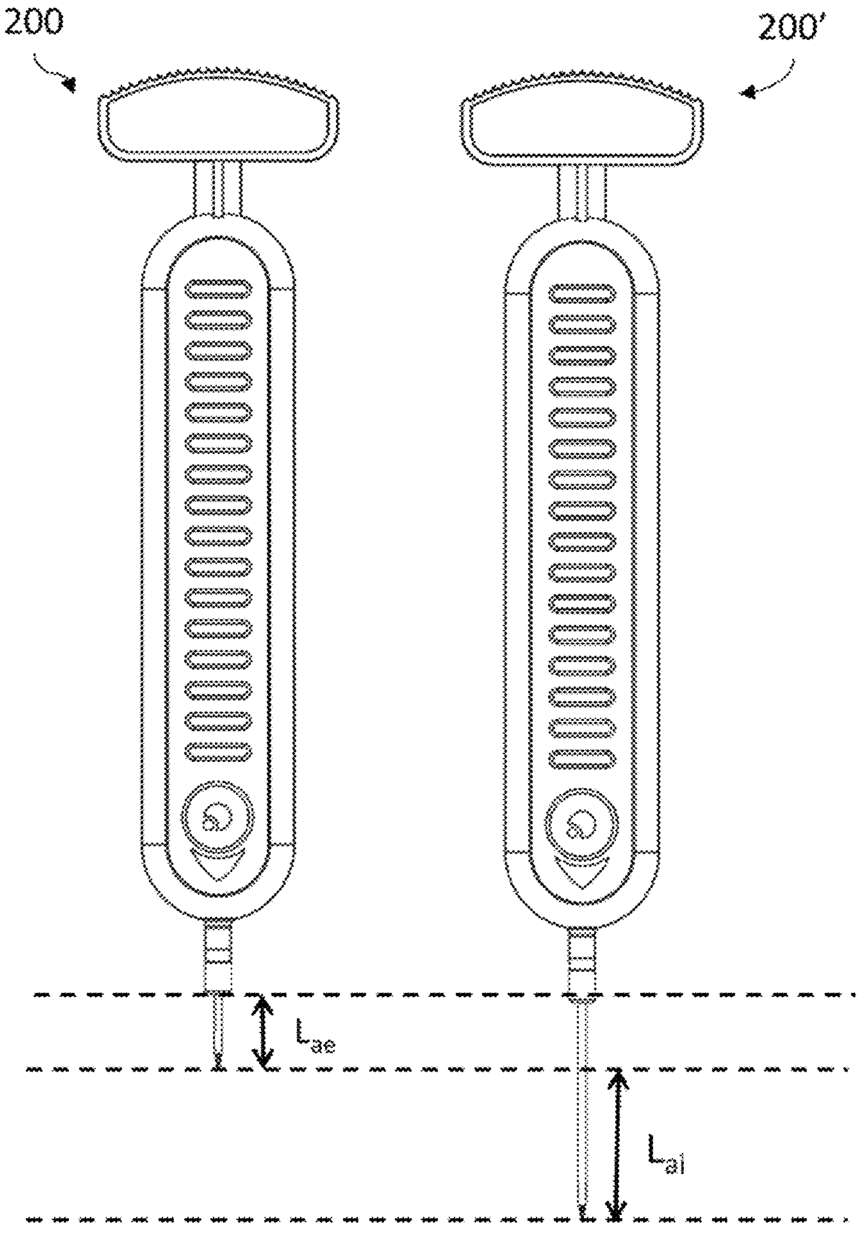
FIG. 10 are non-limiting elevated views of device 200 for generating a channel in an eye tissue layer of FIG. 2 using an ab externo approach and a variant 200' for generating a channel in an eye tissue layer of FIG. 2 using an ab interno approach, in accordance with embodiments of the present disclosure.

FIG. 2 and FIG. 10 illustrate non-limiting implementations of a medical device that is arranged and configured in accordance with certain features, aspects, and advantages of the present disclosure. The illustrated medical device can be used for generating a channel in tissue layer, in particular a drainage channel in an eye tissue layer, or can be any other type of medical device that would benefit from any or all of the later described features, aspects and advantages of the present disclosure.

The term "tissue layer," as used herein, encompasses both a single tissue layer and a collection of layers, such as adjacent stacked layers (a multilayer) or distinct layers. However, the default interpretation typically refers to a single tissue layer. Additionally, when referring to a "tissue layer," it often pertains to a tissue wall characterized by a specific thickness and two sides (outer and inner, or proximal and distal). In this context, the channel or hole created extends between these two sides of the tissue wall. To illustrate, the channel could be situated in the sclero-corneal junction of an individual's eye. This application may be employed to address glaucoma by reducing intraocular pressure, achieved through facilitating fluid communication between the anterior chamber of the eye and the interface connecting the episclera and conjunctiva tissues, or subconjunctiva or subtenon area, for example.

In some embodiments, the medical device 200 includes a body 210 for grasping. For example, the body extends along a longitudinal axis Ω, as shown in FIG. 2.

In some embodiments, the body 210 can be formed with first and second housing segments 240, 260. For example, the first and second housing segments 240, 260 may be configured for assembling one onto another through any suitable coupling means.

Figure 3A:
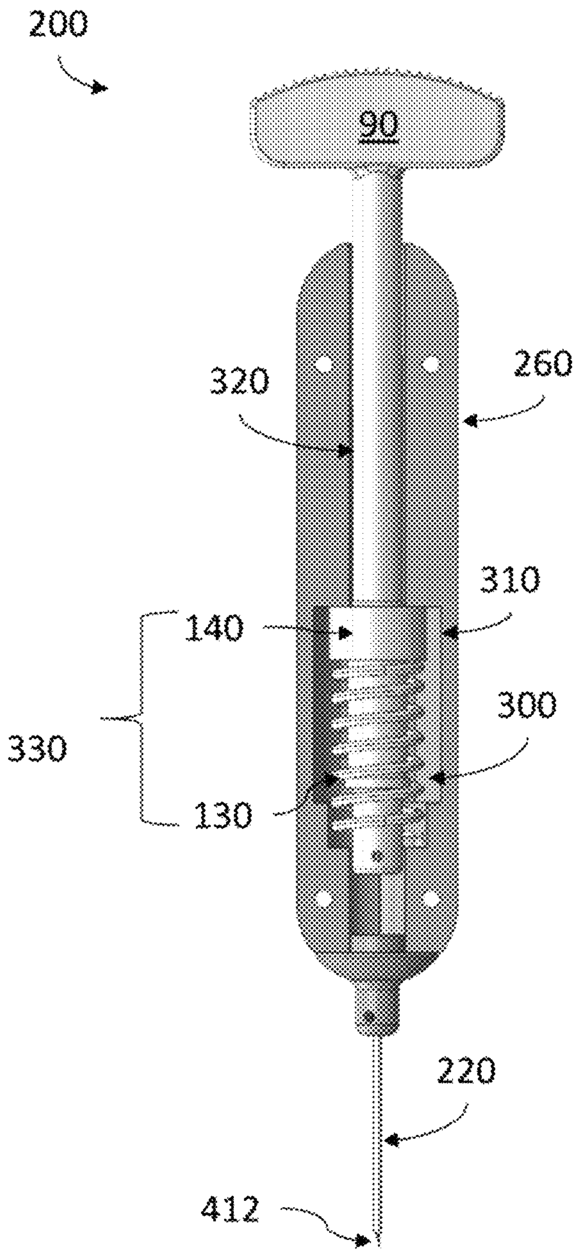
FIG. 3A is a non-limiting cross-section perspective view of an embodiment of the device of FIG. 2 with the actuator in a first position, in accordance with embodiments of the present disclosure.
Figure 3B:
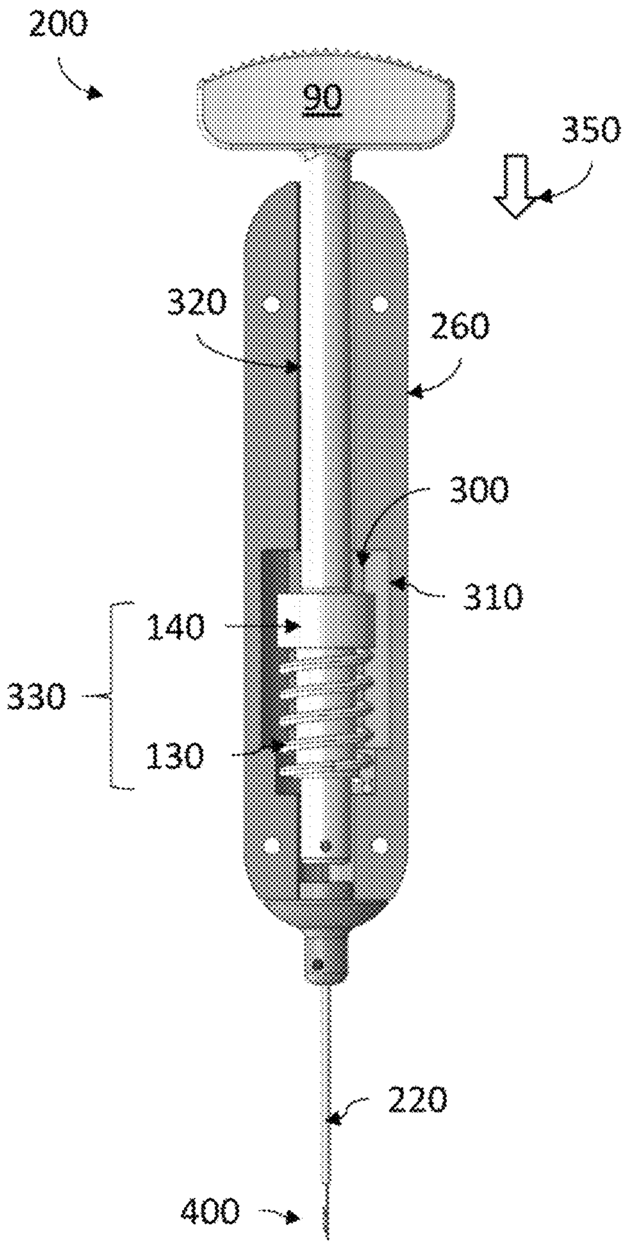
FIG. 3B is a non-limiting cross-section side view of the device of FIG. 3A with the actuator in a second position, in accordance with embodiments of the present disclosure.
Figure 3C:
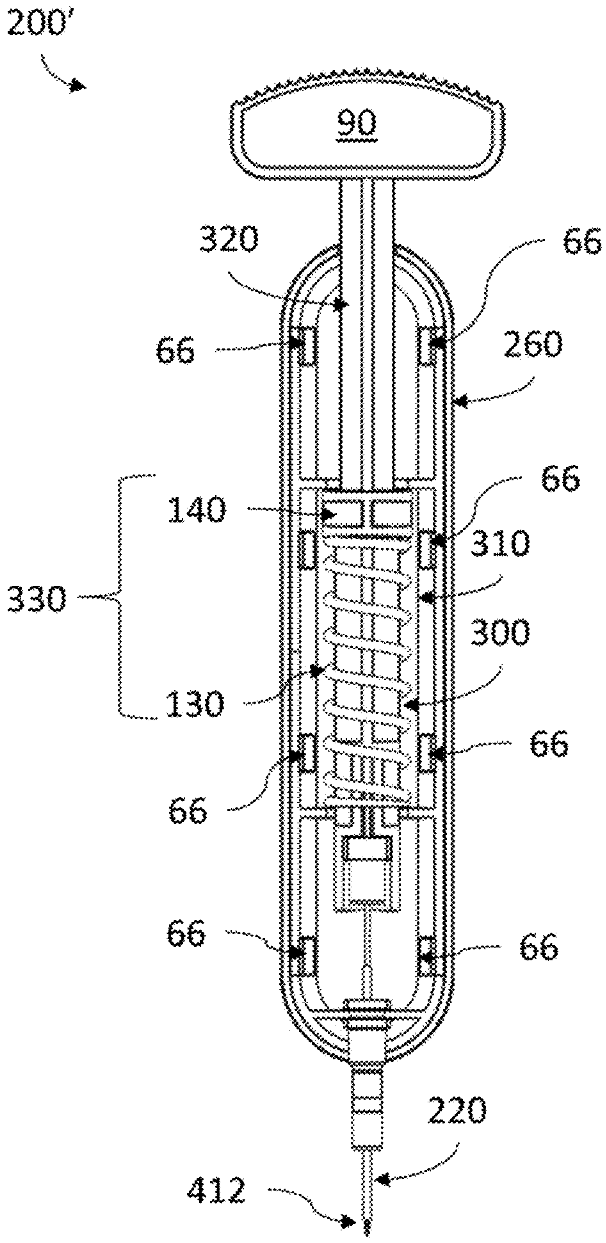
FIG. 3C is a non-limiting cross-section perspective view of another embodiment of the device of FIG. 2 with the actuator in a first position, in accordance with embodiments of the present disclosure.
Figure 3D:
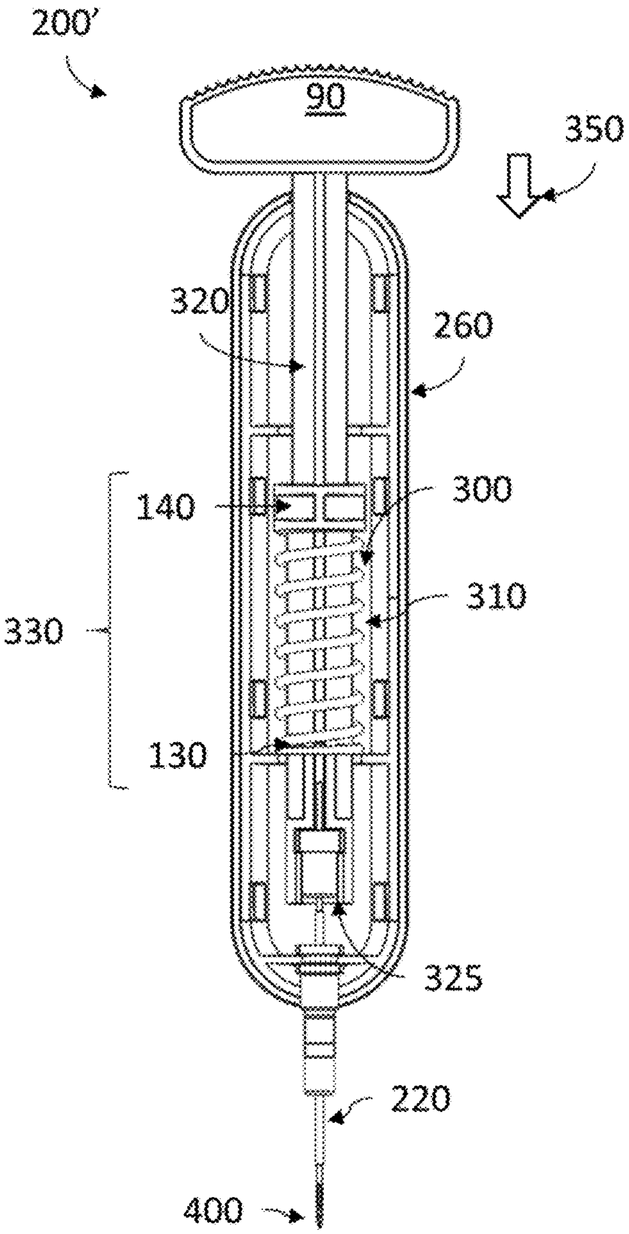
FIG. 3D is a non-limiting cross-section side view of the device of FIG. 3A with the actuator in a second position, in accordance with embodiments of the present disclosure.

As partially shown in FIG. 2 to FIG. 3D, for example, the coupling means may include a plurality of screws 10, which are used to screw together the first and second housing segments 240, 260, thus forming the body 210. In other embodiments, the first housing segment 240 may include a plurality of peripherally spaced projections 66. Correspondingly, the second segment 260 may, accordingly, include a plurality of peripherally spaced notches that receive the corresponding projections 66, so as to assemble the first and second housing segments 240, 260, thus forming the body 210.

In some embodiments, the body 210 may have at least a segment of the surface thereof, which is raised, depressed, grooved, or textured to improve hold by the user or to improve comfort of the user. The user may be a medical practitioner, such as an ophthalmologist.

In some embodiments, the body 210 is capable of being autoclaved or sterilized in some other manner. For example, the body 210 may be made from any suitable material, such as, but not limited to, polyethylene (PE) including low-density PE, high-density PE, or ultra-high molecular weight PE; polypropylene (PP); polytetrafluoroethylene; thermoplastic polyurethane; polycarbonate; polyphthalic acid; acrylic; acrylonitrile butadiene styrene (ABS); silicone, and the like.

In some embodiments, the body 210 may be configured to have a shape that facilitates handling of the medical device 200. For example, during use, the user may grip the medical device 200 with flexion of one or more fingers (e.g., with the middle finger) on a first side of the body 210 and with flexion and opposition of the thumb on a second side of the body 210, the first side being in opposite relationship to the second side.

In some embodiments, the body 210 may have suitable dimensions that facilitate handling of the medical device 200. For example, the body 210 may have a length LD of from about 50 mm to about 150 mm, including any values or ranges therein. For example, a length LD of about 55 mm, about 60 mm, about 65 mm, about 70 mm, about 75 mm, about 80 mm, about 85 mm, about 90 mm, about 95 mm, about 100 mm, about 110 mm, about 120 mm, about 130 mm, about 140 mm, or about 150 mm. For example, a length LD of about 74 mm. For example, the body 210 may have a height H of about 10 mm to about 30 mm, including any values or ranges therein. For example, a height H of about 10 mm, about 15 mm, about 20 mm, about 25 mm, about 30 mm. For example, a height H of about 15 mm. For example, the body 210 may have a depth D of from about 8 mm to about 20 mm, including any values or ranges therein. For example, a depth D of about 8 mm, about 10 mm, about 12 mm, about 14 mm, about 16 mm, about 18 mm, or about 20 mm. For example, a depth D of about 12.5 mm.

The medical device 200 described herein includes components which can be adapted for specific ophthalmologic procedures. As will be apparent to the reader, the components described in the following text are configured to operate to form a drainage channel in an eye, such as a human eye. In some implementations, the medical device 200 may include other components that may benefit from the herein described features and advantages, which can be adapted for similar ophthalmologic procedures.

Piercing Member

In some embodiments, the medical device 200 described herein is equipped with a piercing member to form a channel in a tissue layer. This piercing member can be particularly useful to form a drainage channel in an eye tissue layer.

In a non-limiting practical implementation, the medical device 200 includes piercing member 400. The piercing member 400 can have a proximal portion which is partially housed within a distal end of the medical device 200, as shown in FIG. 2. Details of the piercing member 400 are shown in FIG. 4A to FIG. 4E.

In some embodiments, the piercing member 400 extends along the longitudinal axis Ω.

In some embodiments, the medical device 200 is configured to perform the perforation in the eye tissue layer with the piercing member 400. As will be further discussed later in this text, the medical device 200 is configured to perform such perforation with the piercing member 400 with an axial cutting motion, i.e., there is no rotational movement required.

For example, the perforation includes at least two incisions, which complement each other to form the channel.

Figure 7:
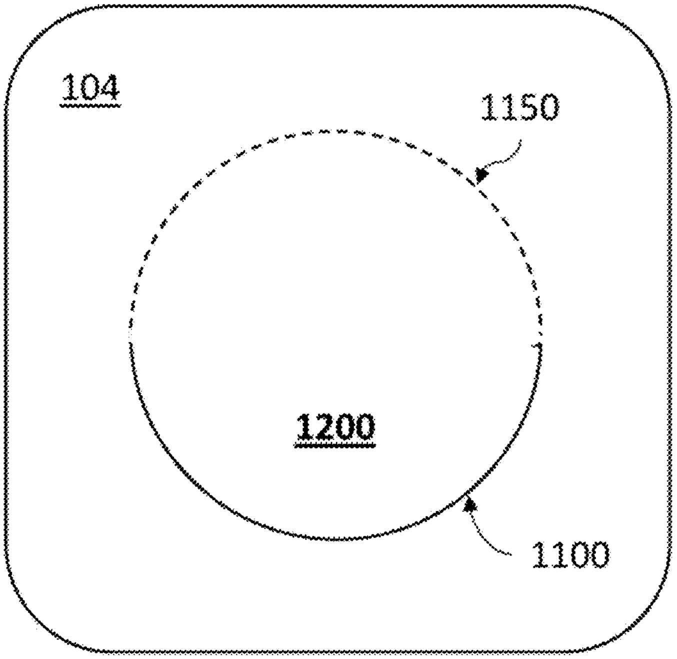
FIG. 7 is a non-limiting side view illustration of a tissue layer with a perforation performed with an ophthalmological procedure for making a drainage channel in a patient eye with the herein described device, in accordance with embodiments of the present disclosure.
Figure 9A:
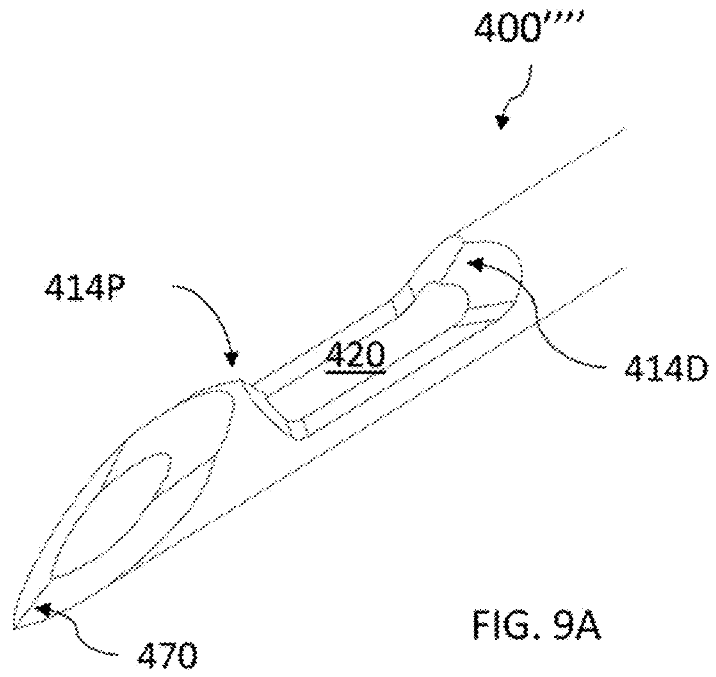
FIG. 9A and FIG. 9B are non-limiting perspective views of different embodiments of the piercing member for use with the medical device of FIG. 2 for making a drainage channel in a patient eye, in accordance with embodiments of the present disclosure.
Figure 9B:
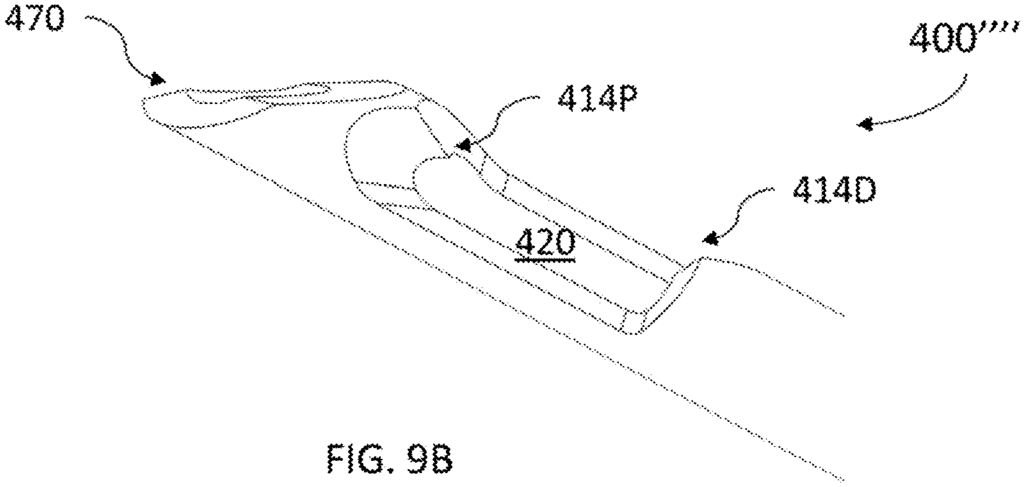

For example, the medical device 200 can be configured to perform with the piercing member 400 a first incision 1100 on a first surface of the tissue layer, for example the sclera 104. For example, the first incision 1100 can be performed by slicing the tissue layer at a first entry point with the piercing member 400, as shown in FIG. 7.

For example, the medical device 200 can be positioned at a first point with respect to the eye and advanced along the longitudinal axis until the piercing member 400 contacts the first surface of the eye tissue layer. Advantageously, the eye tissue layer is intact, i.e., there is no scleral flap. At this point, the piercing member 400 is referred to as being in a first position (relative to the medical device 200 or to components thereof). When the medical device 200 is further advanced towards the tissue layer, then the piercing member 400 performs, from the first position, the first incision 1100. Advantageously, the piercing member 400 is capable of performing the first incision 1100 with a first axial cutting motion. In other words, the cutting motion does not require any rotational movement of the piercing member 400 or of the medical device 200. It will be apparent to the reader in view of the teachings described herein that such axial cutting motion is generally safer relative to cutting motions with rotational movements of existing systems or medical devices that can cause injury to surrounding eye tissue.

For example, the piercing member 400 can be further configured to penetrate into and through the tissue layer, with an axial displacement of the medical device 200 towards the tissue layer. Advantageously, the piercing member 400 is configured to penetrate into and through the tissue layer smoothly and easily with minimum force, therefore it can have a smooth (e.g., polished) outer surface to minimize friction during penetration into and through the tissue layer.

For example, once the piercing member 400 has reached a desired depth into and through the tissue layer, the medical device 200 can be further configured to axially move the piercing member 400, away from the body 210 (or component thereof) to a second position. In use, the medical device 200 moves (extends) the piercing member 400, away from the body 210 (or component thereof) to the second position, while the medical device 200 remains at the same position relative to the eye. Such extension causes the piercing member 400 to position at least a distal segment 412 thereof beyond a second surface of the tissue layer. The first surface and the second surface of the tissue layer are in a spaced apart and opposite relationship to each other, e.g., two sides of a tissue wall, for example of the sclera 104.

For example, the medical device 200 can be configured to perform with the piercing member 400 a second incision 1150 in the second surface of the tissue layer. For example, the second incision 1150 can be performed by slicing the tissue layer at a second entry point with the piercing member 400. For example, each of the first and second entry points can be in a spaced apart relationship to each other.

For example, the medical device 200 can be configured to retract the piercing member 400 towards the body 210 (or component thereof), from the second position to the first position.

The reader will recognize that advantageously, the first and second positions are along the same axis.

In use, the medical device 200 can be configured to retract the piercing member 400 from the second position through the second surface of the tissue layer, performing the second incision 1150 on the second surface of the tissue layer, while the medical device 200 remains at the same position relative to the eye. The retracting motion of the piercing member 400 to the first position further displaces the piercing member 400 into and through the tissue layer, in a direction opposite from that one performed when extending the piercing member 400 away from the body 210 (or component thereof). Displacement of the piercing member 400 into and through the tissue layer in a direction opposite from that one performed when extending the piercing member 400 away from the body 210 (or component thereof) thus completes the perforation 1200 and creates the drainage channel 500.

For example, the first and second incisions 1100, 1150 each can have a shape that complements each other to form a cross section of the perforation 1200. In general, the perforation 1200 represents the cross section of the drainage channel 500. For example, when the drainage channel 500 cross section is substantially circular, the first and second incisions can each form a portion of the complete perforation cross section such that they both form the substantially circular perforation. The medical device 200 described herein thus allows removing a predefined shape of soft tissue segment from an eye tissue layer, resulting in the creation of a corresponding drainage channel 500 with predetermined geometry and orientation between two side walls of the tissue layer. For example, when each of the first and second incisions 1100, 1150 have a half circle shape forming together a circular cross section perforation 1200, the first and second entry points may each include respective apex points 1125, 1175 of the respective half circles, which are in a spaced apart relationship one from another, as shown in FIG. 7.

More details about the piercing member 400 will now be discussed with reference to FIG. 4A to FIG. 4E, and FIG. 9A to FIG. 9B.

In some embodiments, the piercing member 400 includes distal segment 412, which is configured to perform the first incision 1100. For example, the distal segment 412 may include a piercing tip 470, at a distal end thereof, which is configured to slice the tissue layer to perform the first incision 1100. For example, the piercing tip 470 may have a suitable cutting edge geometry such as a bevel tip needle stylet, bevel tip needle cannula, lancet point needle stylet, back bevel needle stylet, back bevel needle cannula, and the like. For example, the piercing tip 470 may have a primary bevel angle $\phi 2$ of from about 15° to about 30°, preferably about 20°.

In some embodiments, the piercing member 400 has an elongated body of any gauge suitable for piercing the tissue layer and form a perforation with a corresponding size sufficient to form a drainage channel of desired size in an eye, such as a human eye. For example, any gauge needle size as set forth in Table 1.

In some embodiments, the piercing member 400 elongated body may have a combination of gauge needle sizes, for example, a larger radius in a proximal portion to increase strength and a reduced radius near a distal portion thereof (e.g., close or at the tip) so as to pierce a small incision in the eye. For example, the piercing member 400 elongated body may have proximal portion size corresponding to a 23GA needle size that is thinned down towards or at the tip to about a 27GA needle size. The reader will understand that any other suitable combination of gauge needle sizes can also be implemented in specific implementations.

Generally, when creating a drainage channel in a patient eye, the medical device 200 is configured to remove the soft tissue segment from the eye.

In some embodiments, the distal segment 412 may further include a medial projection 412P at a proximal end thereof. The medial projection 412P is configured to contact the second surface of the tissue layer, when the medical device 200 retracts the piercing member 400 towards the body 210. The medial projection 412P includes a puncturing edge such that the retracting motion of the piercing member 400 towards the body 210 initially causes the medial projection 412P to perform the second incision 1150 in the tissue layer. The retracting motion of the piercing member 400 towards the body further drives the medial projection 412P into and through the tissue layer, thus completing the perforation. When completing the perforation, the piercing member 400 cuts and removes a soft tissue segment out from the tissue layer to form the drainage channel 500.

In some embodiments, the medial projection 412P may have acute edges each forming an angle $\phi 1$ of about from 25° to about 45° relative to the axis $\chi$ crossing the tip of the medial projection 412P and extending through the piercing tip 470, including any value therein. For example, an angle $\phi 1$ of about 25°, about 30°, or about 35°.

In some embodiments, the piercing tip 470 and the medial projection 412P are aligned along respective first longitudinal axis α and second longitudinal axis β, which are parallel to each other.

In some embodiments, the piercing member 400 elongated body may have a proximal segment 414 that is connected to the distal segment 412 via connecting wall 416. For example, the connecting wall 416 can form a sloping edge over at least a portion thereof between the distal segment 412 and the proximal segment 414. Presence of such sloping edge can reduce stress points in bending when introducing the piercing member 400 into the tissue layer.

In some embodiments, the connecting wall 416 can be configured to define an open cavity 420 nested between a distal edge 414D of the proximal segment 414 and a proximal edge 412E of the distal segment 412. Such open cavity 420 may be configured to receive at least a portion of the soft tissue segment being removed from the tissue layer, preferably all of the soft tissue segment being removed.

For example, the proximal edge 412E can be located at the base of the medial projection 412P.

Figure 4A:
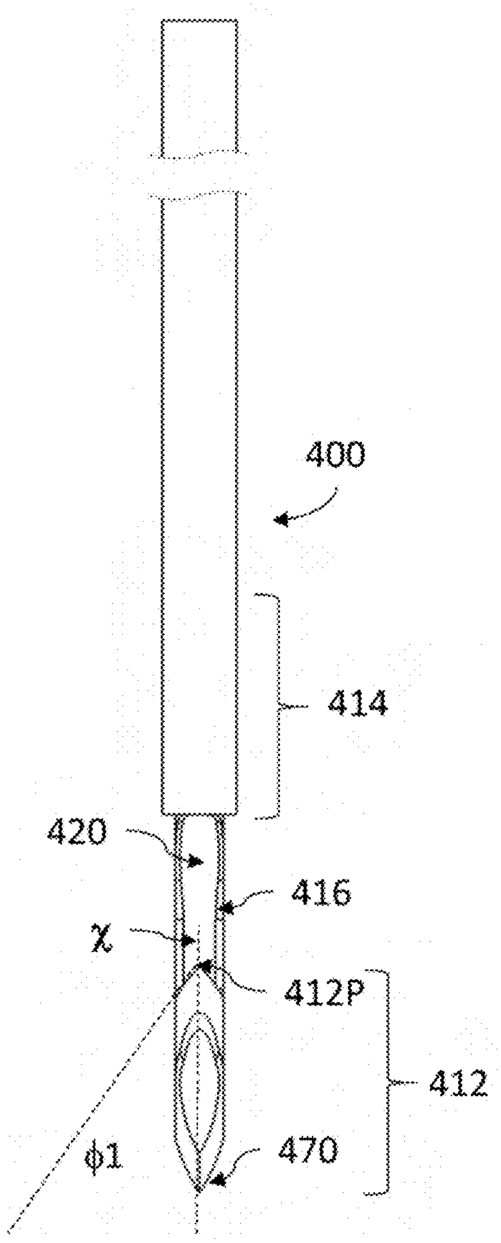
FIG. 4A to FIG. 4E are non-limiting views of a piercing member for use with the device of FIG. 2 for making a drainage channel in a patient eye, in accordance with embodiments of the present disclosure.
Figure 4B:
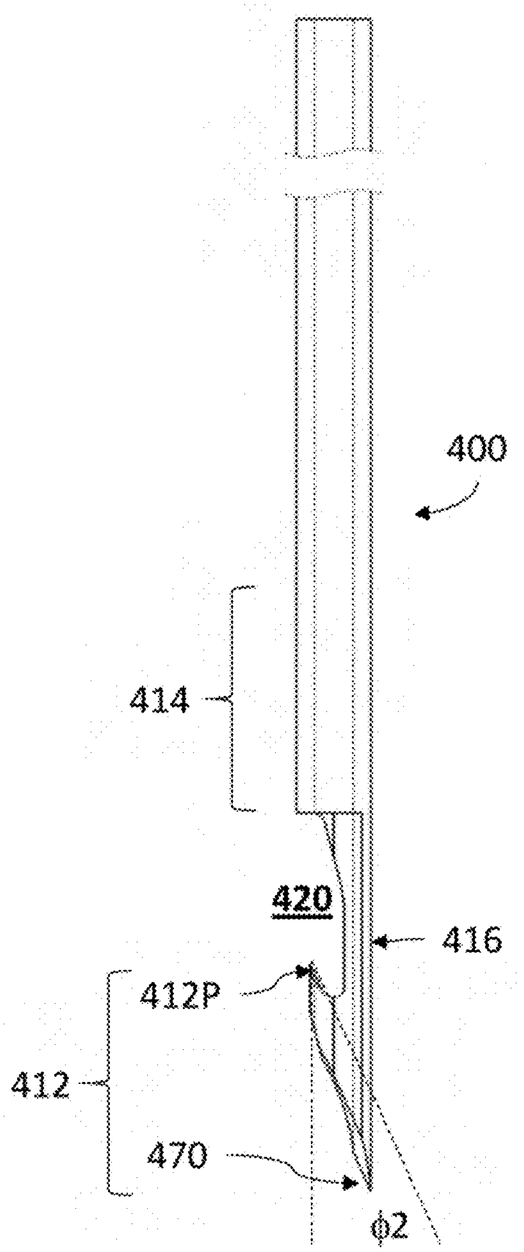
Figure 4C:
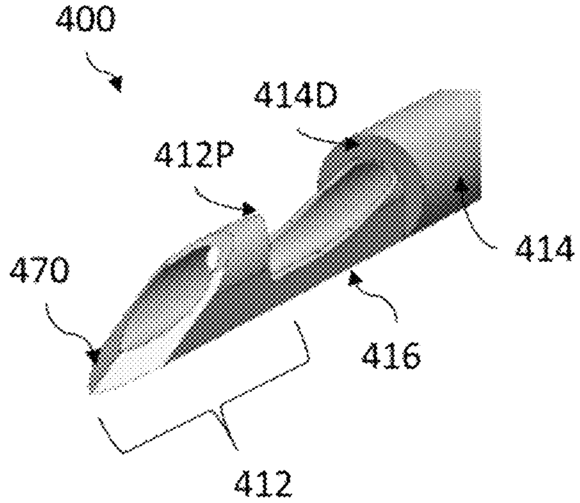
Figure 4D:
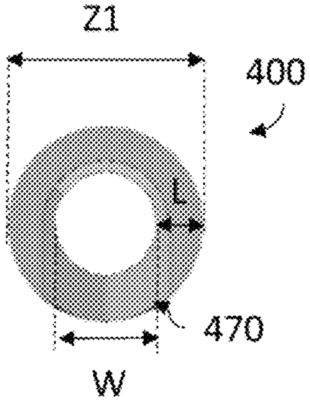
Figure 4E:
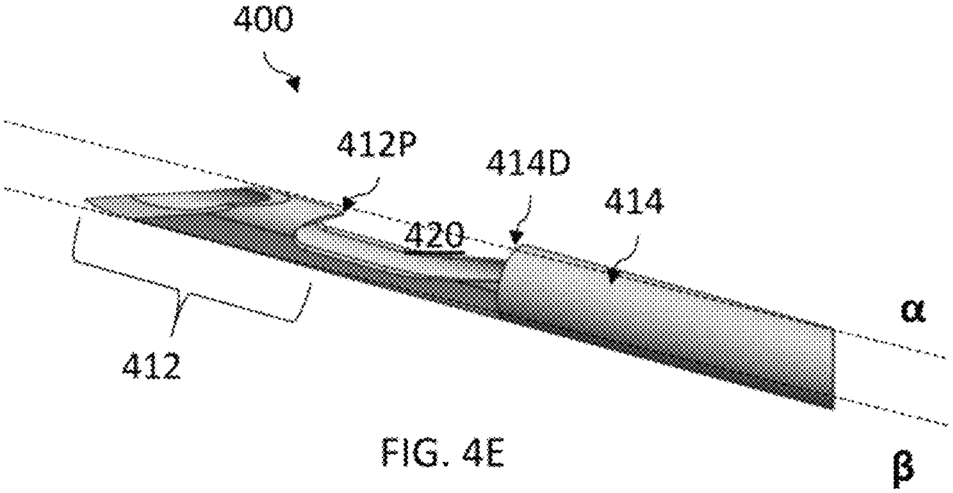

In some embodiments, the piercing member 400 elongated body or portions thereof (e.g., the distal segment 412) may have a cylindrical shape with a circular (round) or substantially circular transverse outer cross section, as shown in FIG. 4D. For example, the piercing member 400 elongated body can have a shape corresponding to the desired drainage channel cross section. For instance, when the piercing member 400 has an elongated body with a circular (round) or substantially circular transverse outer cross section, the resulting drainage channel 500 cross section has a circular (round) or substantially circular shape 1200, as shown in FIG. 7.

In some embodiments, the piercing member 400 elongated body or portions thereof (e.g., the distal segment 412) can be hollow over at least a segment thereof. In other embodiments, the piercing member 400 elongated body or portions thereof (e.g., the distal segment 412) can be hollow over the entire length thereof. In other embodiments, the piercing member 400 elongated body or portions thereof (e.g., the distal segment 412) is solid (i.e., not hollow).

In some embodiments, the piercing member 400 elongated body is configured to penetrate the tissue layer over at least a segment length thereof. For example, the piercing member 400 elongated body may have a length of any suitable size for creating a drainage channel in an eye, such as a human eye. For example, the piercing member 400 elongated body may have a length of from about 20 mm to about 60 mm, including any values or ranges therein. For example, a length of about 20 mm, about 25 mm, about 30 mm, about 35 mm, about 40 mm, about 45 mm, about 50 mm, about 55 mm, or about 60 mm. For example, for performing an ab externo procedure, the piercing member 400 elongated body may have a length of about 30 mm, about 35 mm, or about 40 mm.

In some embodiments, the piercing member 400 includes an elongated body or portions thereof (e.g., the distal segment 412) that is configured to perform a perforation into the tissue layer to obtain a channel of desired size. The piercing member 400 elongated body can have dimensions corresponding a needle gauge as set forth in Table 1:

TABLE 1

| Needle gauge | Outer diameter (inches) | Outer diameter (mm) | Inner diameter (inches) | Inner diameter (mm) |
|---|---|---|---|---|
| 7 | 0.180 | 4.572 | 0.150 | 3.810 |
| 8 | 0.165 | 4.191 | 0.135 | 3.429 |
| 9 | 0.148 | 3.759 | 0.118 | 2.997 |
| 10 | 0.134 | 3.404 | 0.106 | 2.692 |
| 11 | 0.120 | 3.048 | 0.094 | 2.388 |
| 12 | 0.109 | 2.769 | 0.085 | 2.159 |
| 13 | 0.095 | 2.413 | 0.071 | 1.803 |
| 14 | 0.083 | 2.108 | 0.063 | 1.600 |
| 15 | 0.072 | 1.829 | 0.054 | 1.372 |
| 16 | 0.065 | 1.651 | 0.047 | 1.194 |
| 17 | 0.058 | 1.473 | 0.042 | 1.067 |
| 18 | 0.050 | 1.270 | 0.033 | 0.838 |
| 19 | 0.042 | 1.067 | 0.027 | 0.686 |
| 20 | 0.03575 | 0.9081 | 0.02375 | 0.603 |
| 21 | 0.03225 | 0.8192 | 0.02025 | 0.514 |
| 22 | 0.02825 | 0.7176 | 0.01625 | 0.413 |
| 22s | 0.02825 | 0.7176 | 0.006 | 0.152 |
| 23 | 0.02525 | 0.6414 | 0.01325 | 0.337 |
| 24 | 0.02225 | 0.5652 | 0.01225 | 0.311 |
| 25 | 0.02025 | 0.5144 | 0.01025 | 0.260 |
| 26 | 0.01825 | 0.4636 | 0.01025 | 0.260 |
| 26s | 0.01865 | 0.4737 | 0.005 | 0.127 |
| 27 | 0.01625 | 0.4128 | 0.00825 | 0.210 |
| 28 | 0.01425 | 0.3620 | 0.00725 | 0.184 |
| 29 | 0.01325 | 0.3366 | 0.00725 | 0.184 |
| 30 | 0.01225 | 0.3112 | 0.00625 | 0.159 |
| 31 | 0.01025 | 0.2604 | 0.00525 | 0.133 |

For example, the piercing element 400 may have a 27G needle size.

In some embodiments, the piercing member 400 includes proximal segment 414 and distal segment 412, where the distal segment 412 includes piercing tip 470 at a distal end thereof. The piercing member 400 is configured to reciprocate from a stored position to an extended position. In the stored position, the proximal segment 414 is retracted within a lumen of a distal stabilizer element 220 (described elsewhere in this text) and the piercing tip 470 extends outwardly from the stabilizer. In the extended position, at least a portion of the proximal segment 414 and the distal segment 412 extend outwardly from the stabilizer.

FIG. 8A to FIG. 8C illustrate variants 400', 400'', 400''' of piercing member 400. FIG. 8A to FIG. 8C illustrate 400', 400'', 400''' with corresponding stabilizing element 200 (which will be described later in this text). Such variants retain a combination of features that are suitable for performing the herein described perforation into a tissue layer to obtain a channel of desired size. Notably, the cavity 420 may be defined between two cutting edges 412P and 414D.

For example, the piercing member 400 elongated body or portions thereof (e.g., the distal segment 412) may have an external diameter size Z1 of from about 0.050 mm to about 3.000 mm, including any values or ranges therein. For example, an external diameter size Z1 of about 0.050 mm, about 0.100 mm, about 0.150 mm, about 0.200 mm, about 0.250 mm, about 0.300 mm, about 0.350 mm, about 0.400 mm, about 0.425 mm, about 0.450 mm, about 0.475 mm, about 0.500 mm, about 0.600 mm, about 0.700 mm, about 0.750 mm, about 0.800 mm, or about 1.000 mm. For example, an external diameter size Z1 of about 0.630 mm, about 0.640 mm, or about 0.650 mm.

For example, the piercing member 400 elongated body or portions thereof (e.g., the distal segment 412) may have an internal diameter size W of from about 0.040 mm to about 0.075 mm, including any values or ranges therein. For example, an inner diameter size W of about 0.040 mm, about 0.045 mm, about 0.050 mm, about 0.055 mm, about 0.060 mm, about 0.065 mm, about 0.070 mm, or about 0.075 mm. For example, an inner diameter size W of about 0.060 mm, about 0.065 mm, or about 0.070 mm.

In some embodiments, the piercing member 400 elongated body or portions thereof (e.g., the distal segment 412) may have wall thickness L of any suitable size. For example, a wall thickness L of from about 0.050 mm to about 0.400 mm, including any values therein. For example, a wall thickness L of about 0.050 mm, about 0.100 mm, about 0.150 mm, about 0.200 mm, about 0.250 mm, about 0.280 mm, about 0.300 mm, about 0.320 mm, about 0.340 mm, or about 0.360 mm. For example, a wall thickness L of about 0.300 mm, about 0.320 mm, or about 0.340 mm.

In some embodiments, the open cavity 420 may have a length as measured between the distal edge 414D of the proximal segment 414 and proximal edge of the distal segment 412 of any suitable size to receive and accommodate the soft tissue segment. For example, a length of from about 1.50 mm to about 2.50 mm, including any values therein. For example, a length of about 2.00 mm, about 2.10 mm, or about 2.20 mm.

In some embodiments, the open cavity 420 may have a transversal height of any suitable size to receive and accommodate the soft tissue segment. For example, a transversal height of from about 0.200 mm to about 0.350 mm, including any values therein. For example, a transversal height of about 0.220 mm, about 0.240 mm, about 0.260 mm, about 0.280 mm, about 0.300 mm, or about 0.320 mm. For example, a transversal height of about 0.260 mm, about 0.280 mm, or about 0.300 mm.

In some embodiments, the piercing member 400 components can be made from a sufficiently hard, tough, material that is rigid and does not bend when pushed/inserted/progressed through the tissue layer. For example, the piercing member 400 components can be made from any medical-grade material, such as for example medical-grade metal such as medical-grade tungsten, titanium, stainless steel, copper, cobalt chrome, aluminum, magnesium, or any alloys thereof; medical grade plastic, and the like. Preferably, nitinol (nickel titanium alloy), 17-7 PH Stainless (Chromium-Nickel-Aluminum, austenitic stainless steel), or 400 Series Stainless.

In some embodiments, the piercing member 400 can be produced through laser ablation. Advantageously, the piercing member 400 can be coated with a non-stick coating to minimize or avoid sticking to eye tissue during use. For example, the piercing member 400 can be coated with a polytetrafluoroethylene (PTFE) coating to improve cutting and penetrating performance of the piercing member 400.

Distal Stabilizer Element

In a non-limiting practical implementation, the medical device 200 further includes a distal stabilizer element 220, which is coupled to and extends from the distal end of the body 210 along longitudinal axis Ω.

In some embodiments, when in the assembled state, the medical device 200 is configured such that the distal stabilizer element 220 houses a segment of the piercing member 400, such that the distal stabilizer element 220, the piercing member 400, and the body 210 are aligned along or coaxial with the longitudinal axis Ω, as shown in FIG. 1.

In some embodiments, the distal stabilizer element 220 can house a segment of the piercing member 400 when the piercing member is in the first position, as shown in FIG. 3A and FIG. 3C. In such embodiment, the distal segment 412 is advantageously exposed and extends distally in a longitudinal direction, away from the distal stabilizer element 220. Being exposed, allows the distal segment 412 to perform the first incision 1100 as the medical device 200 progresses axially (i.e., axial displacement) towards the tissue layer.

In some embodiments, the distal stabilizer element 220 includes a distal end 225, as shown in FIG. 8A1 to FIG. 8C1. The distal end 225 is configured to abut against the first surface of the tissue layer, as the piercing member 400 is distally advanced into and through the tissue layer to a desired depth. Such a configuration may allow for stabilizing or guiding of the medical device 200 during the ophthalmological procedure, for example.

When performing an ab externo procedure, the distal end 225 is configured to abut against the external surface of the tissue layer, such as the external surface of the eye sclera 104, when the piercing member 400 is distally advanced into and through the tissue layer to a desired depth.

When performing an ab interno procedure, the distal end 225 is configured to abut against the internal surface of the tissue layer, such as the internal surface of the eye sclera 104, when the piercing member 400 is distally advanced into and through the tissue layer to a desired depth. An "ab interno" procedure on the sclera refers to a surgical technique where a surgeon accesses the sclera 104 from inside the eye 50, through a small incision at the edge of the cornea, rather than making an external incision through the conjunctiva and sclera ("ab externo"); essentially, working "from inside" the eye to reach the sclera.

As shown in FIG. 3B and FIG. 3D, the medical device 200 is further configured to distally extend the piercing member 400, outwardly from the distal stabilizer element 220, i.e., away from the distal end of the body 210. For example, away from the distal end 225 of the distal stabilizer element 220. For example, this distal extension can be performed over the longitudinal axis Ω. In use, the piercing member 400 can be distally extended as such by actuating a control point when the piercing member 400 has reached a desired depth into the tissue layer from an axial displacement of the medical device 200. This will be discussed in more details elsewhere in this text.

For example, during an ab externo procedure, the desired depth can be determined as being the point when the distal end 225 of the distal stabilizer element 220 abuts against the external surface of the eye tissue layer, such as the external surface of the sclera 104. Conversely, during an ab interno procedure, the desired depth can be determined as being the point when the distal end 225 of the distal stabilizer element 220 abuts against the internal surface of the eye tissue layer.

In some embodiments, the distal stabilizer element 220 components can be made from any medical-grade material, such as for example medical-grade metal such as medical-grade tungsten, titanium, stainless steel, copper, cobalt chrome, aluminum, magnesium, or any alloys thereof; medical grade plastic, and the like.

In some embodiments, the distal stabilizer element 220 has any suitable dimension for performing the herein described functions. For example, the distal stabilizer element 220 may have any dimension which is suitable for enclosing the piercing element 400 having its own gauge needle dimension.

For example, in some embodiments, the distal stabilizer element 220 may have an outside diameter of from about 0.40 mm to about 1.00 mm, including any values or ranges therein. For example, an outside diameter of about 0.50 mm, about 0.55 mm, about 0.60 mm, about 0.65 mm, about 0.70 mm, about 0.75 mm, about 0.80 mm, about 0.85 mm, about 0.90 mm, about 0.95 mm, or about 1.00 mm. Preferably, an outside diameter of about 0.74 mm.

For example, in some embodiments, the distal stabilizer element 220 may have an internal diameter of from about 0.30 mm to about 0.70 mm, including any values or ranges therein. For example, an internal diameter of about 0.30 mm, about 0.35 mm, about 0.40 mm, about 0.45 mm, about 0.50 mm, about 0.55 mm, about 0.60 mm, about 0.65 mm, about 0.70 mm. Preferably, an internal diameter of about 0.57 mm.

For example, in some embodiments, the distal stabilizer element 220 may have a length of from about 10 mm to about 30 mm, including any values or ranges therein. For example, a length of about 10 mm, about 15 mm, about 20 mm, about 25 mm, or about 30 mm.

For example, for performing an ab externo procedure, the distal stabilizer element 220 can have a length $L_{ae}$ of from about 10 mm to about 14 mm.

For example, for performing an ab interno procedure, the distal stabilizer element 220 can have a length $L_{al}+L_{ae}$ of from about 24 mm to about 28 mm.

The reader will readily understand that for an ab interno procedure, the distal stabilizer element 220 can have an additional length $L_{al}$ relative to the length $L_{ae}$ of from about 10 mm to about 15 mm, such as about 12 mm, about 13 mm, about 14 mm, or about 15 mm.

As mentioned above, the piercing element 400 may have a gauge needle dimension, which is sufficiently small to be able to perform reciprocal movement within the lumen of the distal stabilizer element 220.

Actuator Assembly

In a non-limiting practical implementation, the medical device 200 further includes an actuator assembly configured to cause axial displacement movement of the piercing member 400, such to perform reciprocal movement within the lumen of the distal stabilizer element 220. For example, the actuator assembly may include any suitable component or combination of components capable of providing the functionality described herein. While the following text describes particular implementations of an actuator assembly with reference to the figures, the reader will nevertheless understand that variations may be used to achieve a similar result.

In some embodiments, the medical device 200 actuator assembly includes members that rotate and/or translate relative to one another in a manner proportional to the axial displacement movement of the piercing member 400.

FIG. 3A to FIG. 3D illustrate a non-limiting practical implementation of the actuation assembly, which includes suitable component or combination of components capable of providing the functionality described herein. For example, the actuation assembly includes a control point, which can be engaged by the user to cause axial displacement movement of the piercing member 400.

For example, the axial displacement movement of the piercing member 400 can allow the piercing member 400 to move from a retracted first position (FIG. 3A and FIG. 3C) to an extended second position (FIG. 3B and FIG. 3D) relative to a distal end of the body 210 or to a distal end 225 of the distal stabilizer element 220. For example, the extended position may be one where a segment of the piercing member 400 extends distally away from the distal end of the body 210 (or to the distal end 225 of the distal stabilizer element 220) such that the distal segment 412, the medial projection 412P and the open cavity 420 are visible to the user. For example, the retracted position may be one where the piercing member 400 is at least partially contained within an internal cavity of the distal stabilizer element 220 such that the open cavity 420, and optionally the medial projection 412P, is (are) not visible to the user.

In some embodiment, the control point can take the form of an actuator 90. For example, the actuator 90 can be conveniently located on a proximal portion of the body 210 for ease of access with a finger, preferably the index.

In some embodiments, the actuator 90 may be a slider, trigger, wheel, or any other form that can be easily actuated, preferably with only one finger, such as the index.

In some embodiments, the actuator 90 may include teeth, or some other form that is capable of providing friction, such as along an edge thereof to improve the user's ability to confidently contact, actuate (e.g., push), and release the actuator 90 even when moisture is present or when the user is wearing gloves. Furthermore, to improve the safety of using the medical device 200, the actuator 90 may include a locking mechanism or a means of preventing the unintended activation or release of said actuator.

In some embodiments, the body 210 includes an internal surface 310 defining an internal cavity 300 therein. The internal cavity 300 encloses internal components of the actuator assembly that allow the axial displacement movement of the piercing member 400.

In some embodiments, the actuator assembly is configured to operatively couple the actuator 90 to the piercing member 400. For example, the actuator assembly may include a stem 320 extending through the internal cavity 300, where the stem 320 is configured to operatively couple the actuator 90 to the piercing member 400. For example, the stem 320 and the actuator 90 may be separate components that cooperate to cause the piercing member 400 to axially move along the longitudinal axis Ω. In another example, and as shown in FIG. 3A to FIG. 3D, the stem 320 and the actuator 90 are connected such as to transmit the finger movement imparted onto actuator 90 to the piercing member 400. For example, the stem 320 can be coupled to the piercing member 400 through a distal surface element 325 of the stem 320.

In a non-limiting practical implementation, engaging the actuator 90 (e.g., pressing movement shown with arrow 350) from a first position shown in FIG. 3A and FIG. 3C to a second position shown in FIG. 3B and FIG. 3D, relative to the body 210 causes the piercing member 400 to extend along the longitudinal axis Ω in a direction away from the body 210 to the second position, as shown in FIG. 3B. For example, engaging the actuator 90 (e.g., pressing movement shown with arrow 350) from the first position can effectively move the stem 320 connected to the actuator 90 towards the distal end of body 210, which in turn, causes the piercing member 400 to extend along the longitudinal axis Ω in a direction away from the body 210 to the second position. The first and second positions of the actuator 90 may be reversed, such that engaging the actuator 90 from one position to another position effectively moves the stem 320 connected to the actuator 90 towards the distal end of body 210.

In some embodiments, the actuator 90 may be equipped with a locking mechanism which retains the actuator 90 in a locked configuration at the actuated position, even when the user releases the actuator 90. In such embodiments, a second actuation of the actuator 90 releases the locking mechanism and the actuator 90 then is returned to the first position.

In some embodiments, the actuator 90 may be free from the locking mechanism described above such that when the user releases the actuator 90, the actuator 90 is returned to the first position.

In some embodiments, the actuator 90 may be equipped with a return mechanism, which is designed to facilitate, assist or direct the actuator 90 to return to the first position. For example, the return mechanism may include a spring assembly 330 configured to return the actuator 90 to the first position shown in FIG. 3A and FIG. 3C. For example, the spring assembly 330 may include a coil spring 130 that is positioned over and surrounding a distal segment of the stem 320. Upon engaging the actuator 90, a rim structure 140 extending away from the surface of the stem 320 abuts and compresses the coil spring 130 towards the distal end of the body 210. The coil spring 130 is selected to provide sufficient stored energy when it is compressed to facilitate, assist or direct the actuator 90 to return to the first position shown in FIG. 3A and FIG. 3C.

In some embodiments, the actuator 90 may be associated with non-powered means (e.g., such as those illustrated in the drawings) to cause the piercing member 400 to extend and retract along the longitudinal axis Ω.

In some embodiments, the actuator 90 may be associated with powered means (e.g., motorized), which are well known in the art, in order to cause the piercing member 400 to extend and retract along the longitudinal axis Ω.

In some embodiments, the medical device 200 actuator assembly may include a depth-setting mode and a depth-piercing mode for precise and controlled operation. For example, in the depth-setting mode a user selects a desired cutting depth outside the eye using an adjustable depth-setting mechanism. This mechanism can include generic assembly components such as a rotatable dial, a threaded adjustment member, or a slider mechanism, which allows the user to precisely control the position of the piercing member 400. In particular, the generic assembly components can be non-motorized. For instance, a depth-setting member (not shown) can be manipulated-such as dialed, rotated, or translated linearly-relative to the body 210 to set a desired movement distance for the piercing member 400 to extend along the longitudinal axis Ω in a direction away from the body 210. In one example, a threaded interface may allow incremental adjustments, where rotating the depth-setting member in one direction increases the movement distance (depth) and rotating it in the opposite direction decreases the set movement distance. Alternatively, a spring-loaded detent mechanism or a click-stop system may facilitate discrete adjustments. These components ensure that the depth-setting mechanism provides reliable and repeatable precision for the medical procedure.

Once the depth is selected, the medical device 200 is positioned relative to the eye, and the user initiates the depth-piercing mode. This mode can be activated by engaging a control point, such as the actuator 90, which may be a button, lever, switch, slider, or similar activation mechanism. Upon activation, internal component of the actuator assembly, such as a cam system, gear train, or linear drive mechanism, engage to automatically move the piercing member 400 to the pre-set depth along the longitudinal axis Ω, extending outwardly (in a direction away) from the body 210. This ensures precise and controlled coring or incision. The use of generic assembly components such as a non-motorized actuator, spring-loaded drive, tensioned springs, torsion bars, elastic bands, or pneumatic piston ensures smooth and controlled movement, preventing over-extension or deviation from the pre-set depth. Additionally, mechanical stops or guides can be incorporated to provide further control and limit movement to the desired range. This design ensures precise and controlled coring or incision. The two-mode functionality, incorporating a depth-setting mechanism and automated piercing activation, allows for enhanced user control and accuracy. These features support applications requiring highly specific depth adjustments during medical procedures, with the assembly components ensuring compatibility across a variety of configurations and designs.

Ophthalmologic Procedure

In a non-limiting practical implementation of the present disclosure, the medical device described herein can be used to form a drainage channel in an eye. Advantageously, the procedure can be performed using only topical anesthesia in an outpatient clinic, without need for an operating room.

In general, the medical device described herein is designed for use in a method performing a perforation in an eye tissue layer to form a channel using the medical device. For example, the method includes performing a first axial cutting motion on a first surface of the tissue layer to form a first incision, and a second axial cutting motion on a second surface of the tissue layer to form a second incision to complete the perforation and remove a soft tissue segment, the first and second surfaces being on opposite sides of the tissue layer, and the first and second incisions forming together the channel.

Figure 6A:
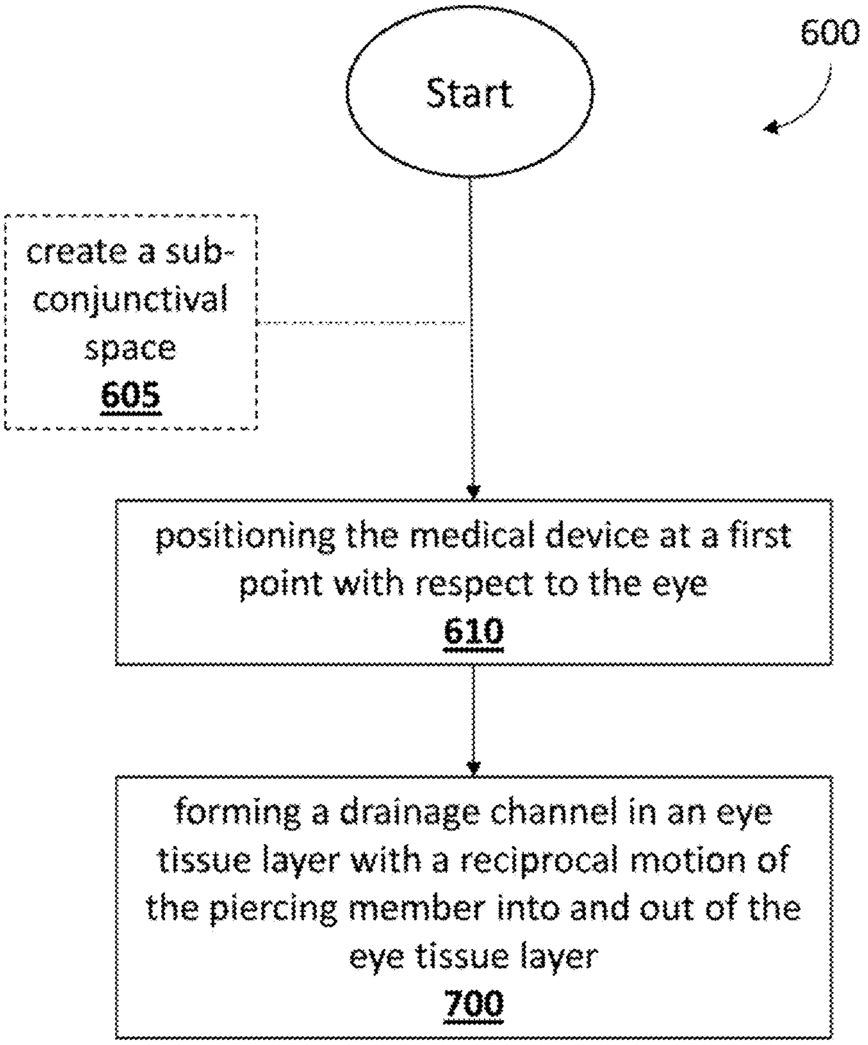
FIG. 6A to FIG. 6C are non-limiting flowcharts illustrating steps of an ophthalmological procedure for making a drainage channel in a patient eye, in accordance with embodiments of the present disclosure.
Figure 6B:
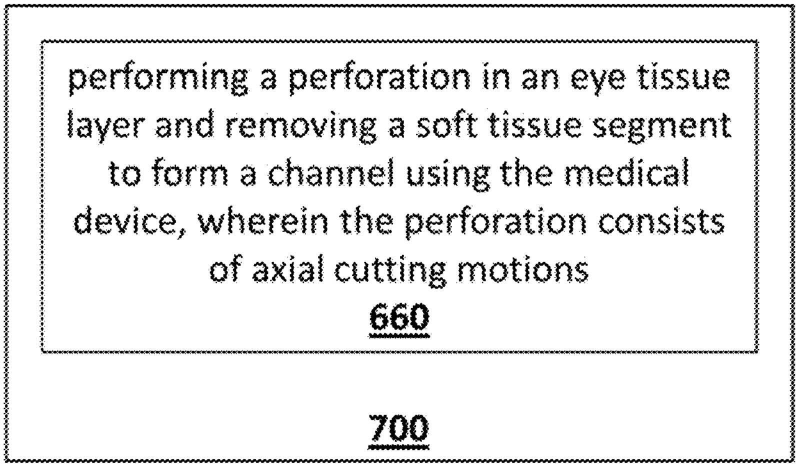
Figure 6C:
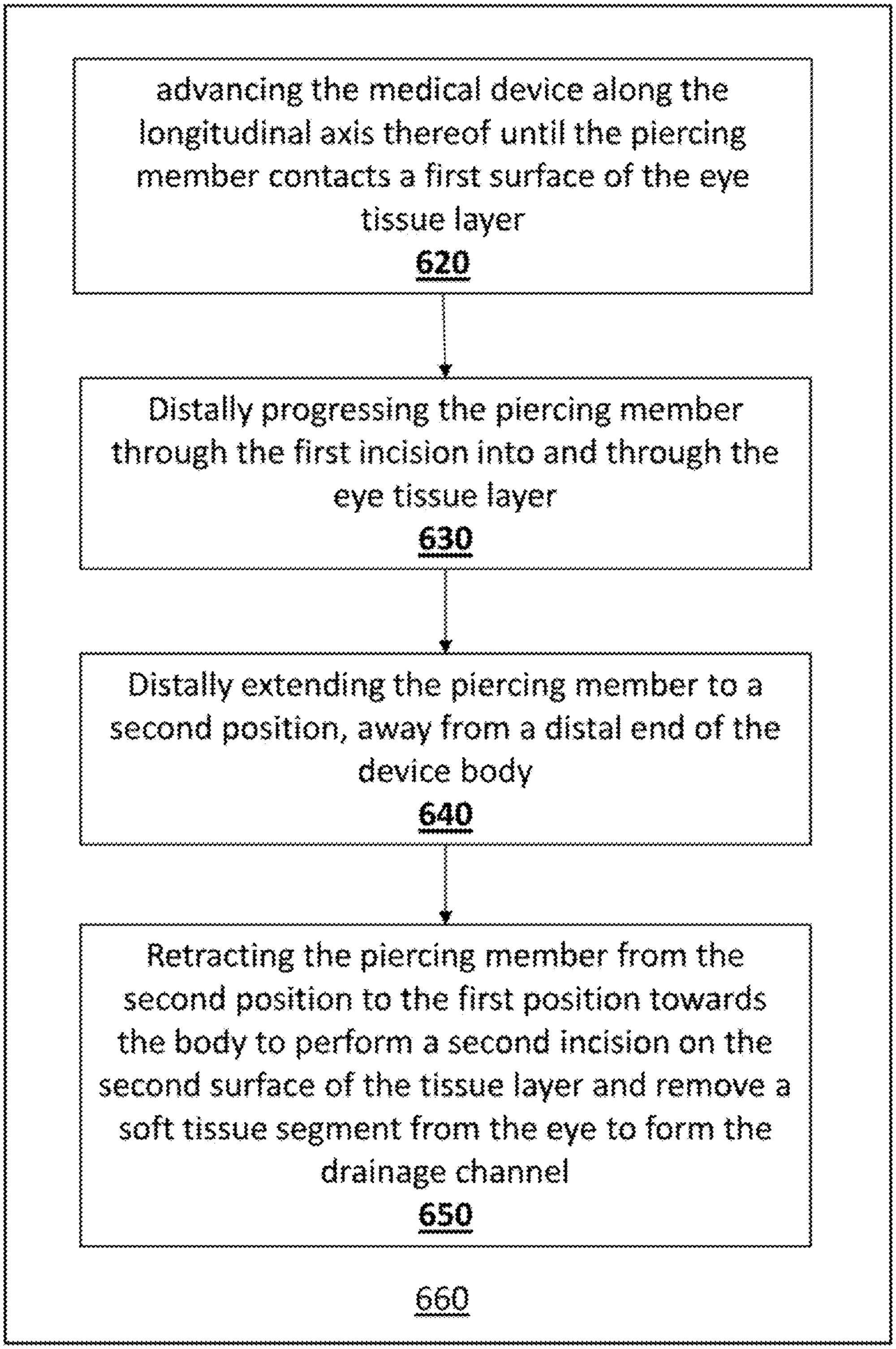

A non-limiting practical implementation is illustrated in the exemplary flowchart of FIG. 6A to FIG. 6C. The method 600 includes a first step 610 of positioning the medical device at a first point with respect to the eye. At step 700, the method 600 includes forming a drainage channel in an eye tissue layer with a reciprocal motion of the piercing member into and out of the eye tissue layer.

For example, forming the drainage channel step 700 may include one or more of the following steps.

For example, at step 660, the method 600 includes performing a perforation in an eye tissue layer and removing a soft tissue segment to form a channel using the medical device, where the perforation consists of axial cutting motions.

For example, the perforation step 660 may include one or more of the following steps.

At step 620, the method 600 can includes advancing the medical device along the longitudinal axis thereof until the piercing member contacts a first surface of the eye tissue layer. At this step, the piercing member 400 is at a first position. For example, the piercing member 400 at the first position can be at least partially housed within the distal stabilizer element 220.

At step 630, the method 600 can further include distally progressing the medical device to cause the piercing member 400 to perform a first incision 1100 in the eye tissue layer with a first axial cutting motion (e.g., the motion being along an axis substantially perpendicular to the tissue layer surface), and progressing the piercing member 400 through the first incision 1100 into and through the tissue layer. Such progression can occur, for instance, until the piercing member 400 has reach a desired depth. For example, the desired depth can be determined as being the moment when the distal end 225 of the distal stabilizer 220 abuts against the first surface of the tissue layer.

At step 640, the method 600 can further include distally extending the piercing member 400 to a second position, beyond the second surface. For example, the piercing member 400 extends to the second position such that the distal segment 412 of the piercing member 400 is distally displaced through the tissue layer. For example, at the second position, the distal segment 412 of the piercing member 400 can have reached the anterior chamber of the eye when the procedure is an ab externo procedure.

At step 650, the method 600 can further include retracting the piercing member 400 from the second position to the first position to perform a second incision 1150 on the second surface of the tissue layer and remove a soft tissue segment from the eye to form the drainage channel. For example, this retracting motion can cause a proximal edge 412P of the distal segment 412 of the piercing member 400 to puncture the second surface and perform the second incision 1150 with a second axial cutting motion. Retracting the piercing member 400 to the first position, further causes the proximal edge 412P of the distal segment 412 of the piercing member 400 to complete the perforation 1200 and remove a soft tissue segment out of the tissue layer, where the soft tissue segment basically has the shape of the drainage channel. The drainage channel hence formed is substantially a scleral drainage channel. For example, the soft tissue segment can be contained within the cavity 420 of the piercing member 400.

In a practical non-limiting implementation, when performing an ab externo procedure, the medical device 200 is positioned at an external point with respect to the eye and advanced along the longitudinal axis thereof until the piercing member 400 contacts the external surface of the sclera 104 tissue layer, the first surface. When the medical device 200 is further advanced towards the tissue layer, then the piercing member 400 performs the first incision 1100 in the external surface of the eye tissue layer, with an axial cutting motion. The medical device 200 is then further advanced towards the tissue layer such that the piercing member 400 penetrates into and through the tissue layer. The medical device 200 then distally extends (e.g., projects) the piercing member 400 away from the body 210 to a second position, such that the piercing member 400 distal segment 412 is positioned beyond the second surface of the tissue layer. The medical device 200 then retracts the piercing member 400 to the first position such that the piercing member 400 retracts towards the second surface of the tissue layer, performing the second incision 1150 on the second surface of the tissue layer. The retracting motion of the piercing member 400 to the first position further displaces the piercing member 400 into and through the tissue layer to complete the perforation 1200 and remove the soft tissue segment. This step helps remove any obstructive tissue, thereby establishing an efficient pathway for the drainage of aqueous humor from the anterior chamber to an external area, such as the subconjunctival or subtenon space, or into a specially created reservoir.

When performing an ab externo procedure, the procedure can be done by entering the eye tissue layer by a distance of about 1.0 to 2.0 mm from the limbus to create a scleral tunnel until the eye anterior chamber.

When performing an ab interno procedure, the procedure can be done by entering the eye anterior chamber 100 and advancing the medical device 200 to contact an internal surface of an eye tissue layer. For example, positioning the piercing member 400 above the trabecular meshwork, near the iridocorneal angle. The piercing member 400 is then directed outward to reach a predetermined point in the subconjunctival space or subtenon space to create a scleral tunnel.

In a practical non-limiting implementation, when performing an ab interno procedure, the procedure begins with a small incision in the cornea, just large enough to accommodate the piercing member 400, for example a size to accommodate a 23-27 gauge needle. This incision provides access to the eye's anterior chamber 100. Before the operation, the eye can be filled with a viscoelastic material, which stabilizes the internal structures and creates space for surgical maneuvers. Next, the piercing member 400 is carefully inserted through this opening into the anterior chamber 100. The medical device 200 is then further advanced along the longitudinal axis until the piercing member 400 contacts the tissue layer on an opposite side of the eye relative to the incision. When the medical device 200 is further advanced towards the tissue layer, then the piercing member 400 performs the first incision 1100 in the internal surface of the eye tissue layer, with an axial cutting motion (i.e., no rotational movement required). The medical device 200 is then further advanced towards the tissue layer such that the piercing member 400 penetrates into and through the tissue layer to reach a predetermined point in the subconjunctival space or subtenon space. The medical device 200 then distally extends (e.g., projects) the piercing member 400 away from the body 210 to a second position, such that the piercing member 400 distal segment 412 is positioned beyond the second surface of the tissue layer. The medical device 200 then retracts the piercing member 400 to the first position such that the piercing member 400 retracts towards the second surface of the tissue layer, performing the second incision 1150 on the second surface of the tissue layer. The retracting motion of the piercing member 400 to the first position further displaces the piercing member 400 into and through the tissue layer to complete the perforation 1200 and remove the soft tissue segment. This step helps remove any obstructive tissue, thereby establishing an efficient pathway for the drainage of aqueous humor from the anterior chamber to an external area, such as the subconjunctival or subtenon space, or into a specially created reservoir. After positioning the device, the viscoelastic material, initially introduced to facilitate the procedure, is meticulously removed through irrigation and aspiration.

The final step may involve the injection of agents like Mitomycin C (MMC) or 5-Fluorouracil (5-FU) into the subconjunctival or subtenon space. These agents enhance the efficacy of the procedure and help reduce potential complications.

Reference is made to FIGS. 5A to 5F exemplifying a non-limiting technique for forming a channel in a tissue layer by using the medical device of the present disclosure. This example forms a channel in a silicone-based mock eye to illustrate an ab externo procedure, i.e., where the device approaches the sclera tissue layer from outside the eye. A segment of the mock eye is shown, where the channel is desired.

Figure 5A:
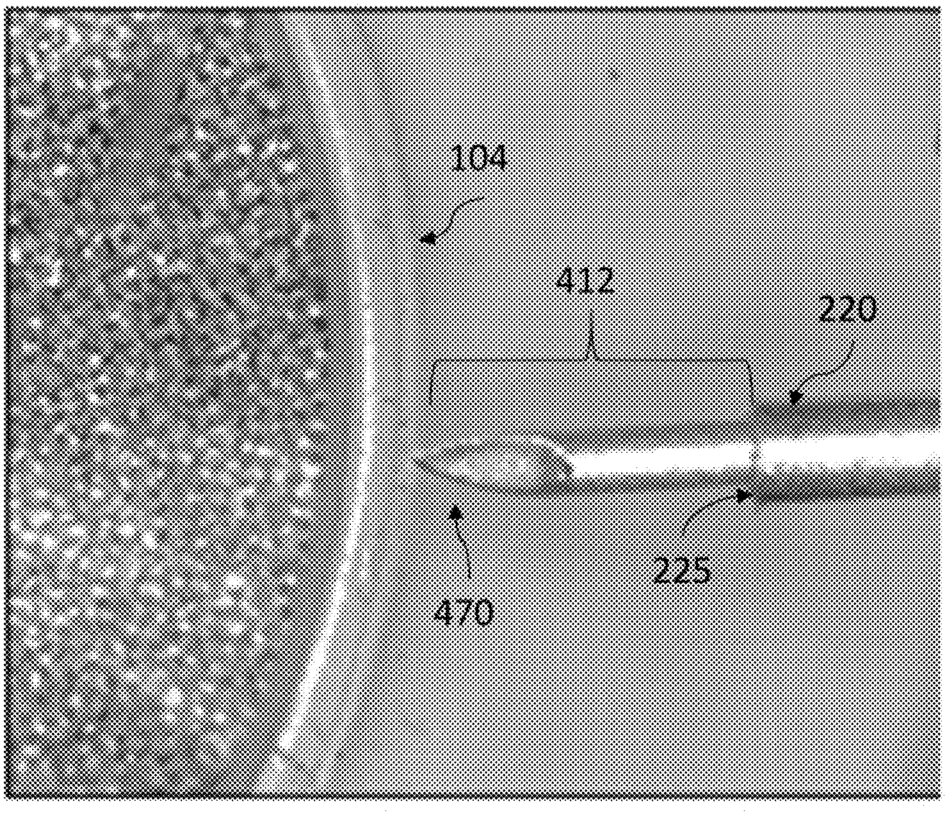
FIG. 5A to FIG. 5D are non-limiting pictures of a mock ophthalmological procedure using a silicone eye model and the device of FIG. 2, in accordance with embodiments of the present disclosure.

As shown in FIG. 5A, the ab externo perforation procedure 600 includes a first step 610 of piercing an external surface of the eye tissue layer (shown as sclera 104) with piercing member 400 to obtain first incision 1100. As discussed previously, the first incision 1100 is performed with a first axial cutting motion. Care should be taken to not yet actuate the actuator 90 at this point, since doing so would otherwise cause the piercing member 400 to prematurely extend away from the distal stabilizer element 220. Piercing the eye tissue layer (shown as sclera 104) is thus performed by positioning the medical device 200 at a first point with respect to the eye, and advancing the medical device 200 along the longitudinal axis until the piercing member 400 contacts an external surface of the eye tissue layer.

Optionally, when performing the ophthalmologic procedure, prior to piercing the sclera 104 with the piercing member 400, the user may wish to create a sub-conjunctival space to separate the conjunctiva from the sclera 104, for example by injecting a suitable solution into the conjunctiva, subconjunctiva space or subtenon space (depending on the ophthalmologist preference), optional step 605 in FIG. 6. For example, by injecting mitomycin-C (MMC) or 5-fluorouracil (5-FU).

Figure 5B:
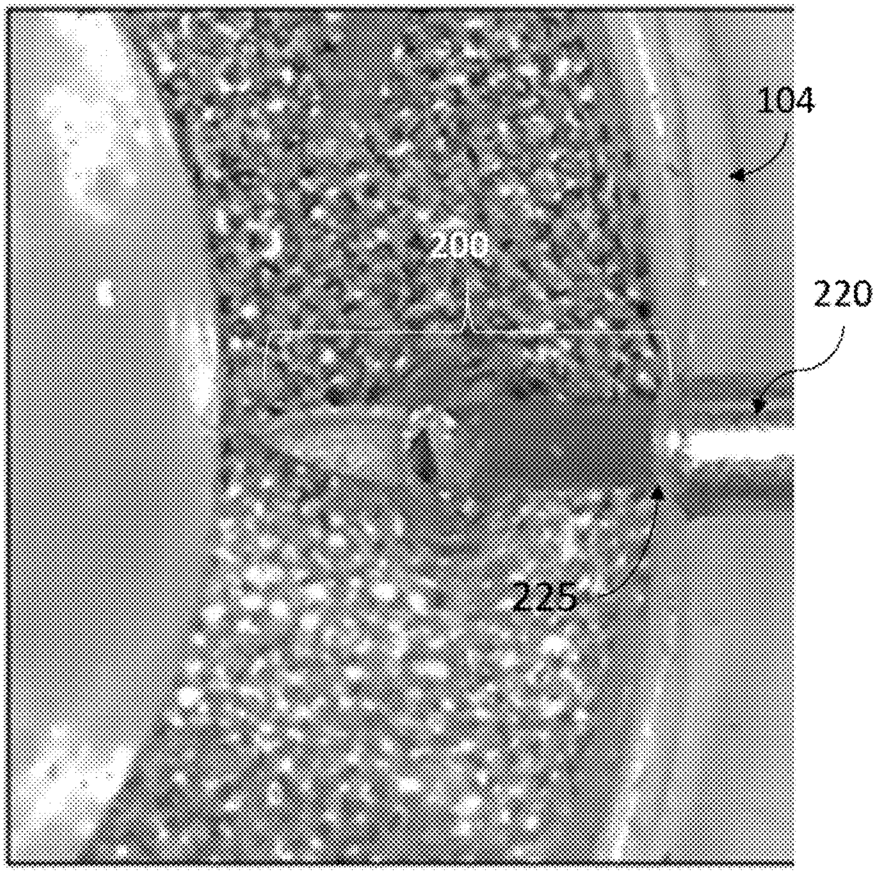

As shown in FIG. 5B, the user then distally progresses the medical device to cause the piercing member 400 to perform the first incision 1100 in the eye tissue layer with the first axial cutting motion. The user then distally progresses the piercing member 400 through the first incision, into and through the eye tissue layer at step 620. For example, distally progressing the piercing member 400 into and through the eye tissue layer can be performed by axial advancement of the medical device 200 such that the piercing member 400 distally progresses into and through the tissue layer. Such axial advancement of the medical device 200 can be performed until the distal stabilizer element 220 distal end 225 abuts on the external surface of the tissue layer, e.g., on the external surface of the sclera 104.

Figure 5C:
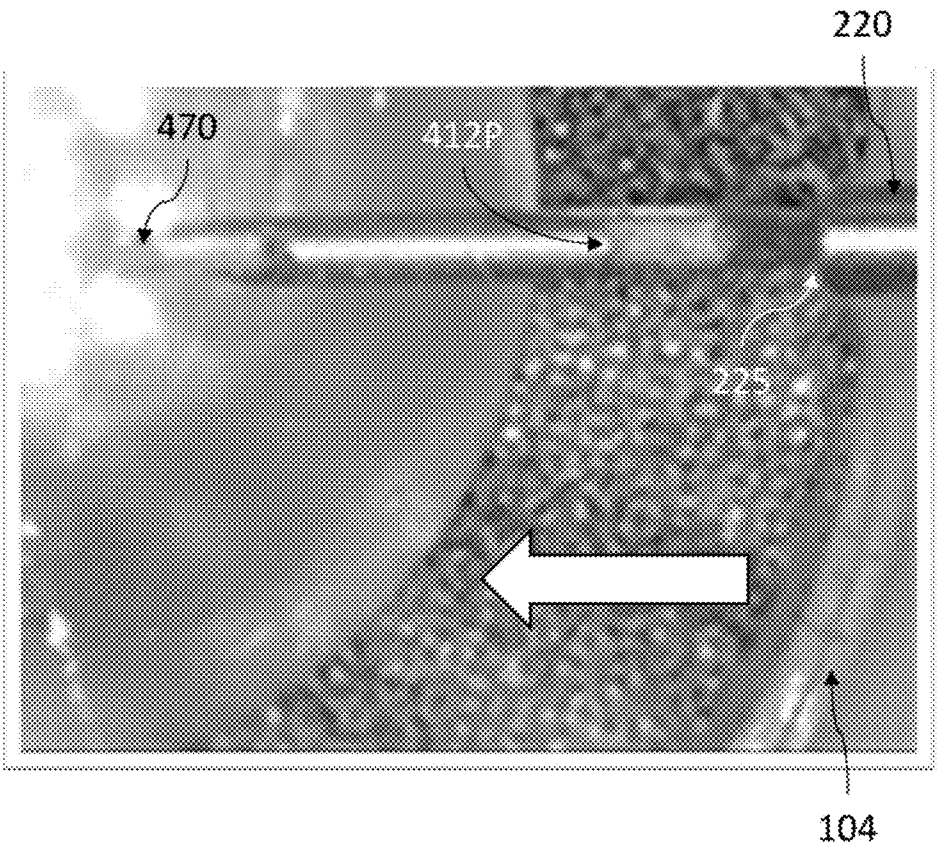

As shown in FIG. 5C, the medical device 200 then distally extends the piercing member 400 to a second position, away from a distal end of body 210, at step 630. For example, this can be performed by engaging the actuator 90 with suitable finger pressure, such as with the index. More particularly, the piercing member 400 is extended to a second position, through the tissue layer, such that the distal segment 412 of the piercing member 400 is distally displaced through the tissue layer. For example, the distal segment 412 of the piercing member 400 is distally displaced through the tissue layer until the proximal projection 412P has completely traveled through the tissue layer beyond the second surface, e.g., through the sclera 104. The reader will understand that in doing so, the piercing tip 470 can also penetrate into the anterior chamber 100. Advantageously, the distal stabilizer element 220 distal end 225 rests on the external surface of the tissue layer throughout this step, which provides safe stability to the medical device 200.

Figure 5D:
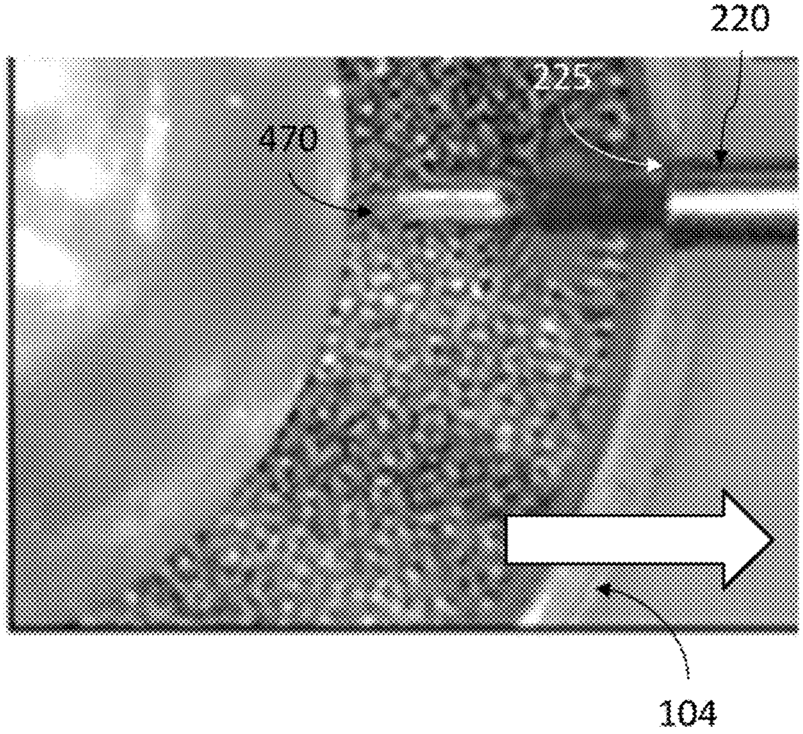

As shown in FIG. 5D, the medical device 200 then retracts the piercing member 400 to the first position, at step 640. For example, the user can do so by releasing the actuator 90. Such retraction of the piercing member 400 causes the proximal projection 412P to retract to the first position. This step causes the proximal projection 412P to perform a second incision 1150 on the internal surface of the tissue layer and through the tissue layer to complete the perforation 1200 and remove the soft tissue segment from the eye. This step creates the drainage channel 500. Preferably, the soft tissue segment being removed is received in the open cavity 420.

In particular, retracting the proximal projection 412P to the first position can be performed while the distal end 225 abuts on the external surface of the sclera 104. The user then withdraws the medical device 200 from the eye.

In some embodiments, the medical device 200 is a single use device which can be discarded after use.

Other examples of implementations will become apparent to the reader in view of the teachings of the present description and as such, will not be further described here.

Note that titles or subtitles may be used throughout the present disclosure for convenience of a reader, but in no way these should limit the scope of the invention. Moreover, certain theories may be proposed and disclosed herein; however, in no way they, whether they are right or wrong, should limit the scope of the invention so long as the invention is practiced according to the present disclosure without regard for any particular theory or scheme of action.

All references cited throughout the specification are hereby incorporated by reference in their entirety for all purposes.

Reference throughout the specification to "some embodiments", and so forth, means that a particular element (e.g., feature, structure, and/or characteristic) described in connection with the invention is included in at least one embodiment described herein, and may or may not be present in other embodiments. In addition, it is to be understood that the described inventive features may be combined in any suitable manner in the various embodiments.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated. For example, a variation of +/−5% is encompassed by the terms "around", "about" or "approximately".

Although various embodiments of the disclosure have been described and illustrated, it will be apparent to those skilled in the art considering the present description that numerous modifications and variations can be made. The scope of the invention is defined more particularly in the appended claims.

What is claimed is:

1. A device for generating a fluid channel in an eye tissue layer, comprising a) a body configured for grasping, the body having an actuator located on a proximal portion thereof, b) a piercing member including a proximal segment and a distal segment, the distal segment including a piercing tip at a distal end thereof, and c) a distal stabilizer element extending from a distal end of the body, the distal stabilizer element including a lumen, wherein the piercing member is configured to be displaced, by actuation of the actuator in a first direction, from (i) a stored position, wherein the proximal segment is retracted within the stabilizer lumen and the piercing tip extends outwardly from the distal stabilizer, to (ii) an extended tissue channel initiation position in which the distal segment of the piercing member pierces a first surface of the eye tissue layer in which a fluid channel is to be formed, wherein the distal segment and at least a portion of the proximal segment extend outwardly from the distal stabilizer, with the piercing member axially displaced distally from the body, wherein the distal segment further includes a medial projection at a proximal end thereof, which includes a puncturing edge oriented in a direction reverse to an insertion direction in the eye tissue layer and extending proximally from the piercing tip, the medial projection configured to contact and cut a second surface of the eye tissue layer when the piercing member is retracted toward the body, the second surface of the eye tissue layer being opposite from the first surface, by actuation of the actuator in a second direction opposite to the first direction, and complete formation of the fluid channel in the eye tissue layer.

2. The device of claim 1, wherein the proximal segment is connected to the distal segment via a connecting wall, wherein the connecting wall is configured to define an open cavity nested between a distal edge of the proximal segment and a proximal edge of the distal segment.

3. The device of claim 2, wherein the open cavity has a length sufficient for receiving a soft tissue segment corresponding to the channel, wherein the length is about 1.50 mm to about 2.50 mm.

4. The device of claim 1, wherein the piercing tip and the medial projection are aligned along respective first and second longitudinal axes, the first and second longitudinal axes being parallel to one another.

5. The device of claim 4, wherein in the stored position, the piercing member is configured to perform a first cutting motion on the first surface of the eye tissue layer using the piercing tip.

6. The device of claim 5, wherein movement of the piercing member from the stored position to the extended position is configured to pierce the tissue layer such that the piercing tip traverses the tissue layer and extends beyond a second surface of the tissue layer, the first and second surfaces being opposite one another.

7. The device of claim 6, wherein movement of the piercing member from the extended position to the stored position is configured to perform a second cutting motion on the second surface of the tissue layer using the medial projection, the first and second cutting motions collectively forming the channel through the tissue layer.

8. The device of claim 7, wherein the first and second cutting motions are coaxial.

9. The device of claim 5, wherein the distal stabilizer element includes a distal end configured to abut against the first surface of the tissue layer.

10. The device of claim 4, wherein the piercing tip includes a bevel tip needle cutting shape geometry.

11. The device of claim 1, wherein the device body includes an internal surface defining an internal cavity, wherein a stem extends through the internal cavity, and wherein the stem is configured to operatively couple the actuator to the piercing member.

12. The device of claim 1, wherein the piercing member has one or more of the following: a length of from about 20 mm to about 50 mm; an external diameter size of from about 0.050 mm to about 3.000 mm; an inner cross section which is substantially circular with an internal diameter size of from about 0.040 mm to about 0.075 mm; and a body with a wall thickness of from about 0.050 mm to about 0.400 mm.

13. The device of claim 1, wherein the piercing member includes a larger radius in a proximal portion and a reduced radius near a distal portion thereof.

14. The device of claim 1, wherein the actuator is equipped with a return mechanism including a spring assembly to facilitate actuation of the actuator in the second direction.

* * * * *